United States Patent
Uggirala et al.

(10) Patent No.: US 12,276,969 B2
(45) Date of Patent: *Apr. 15, 2025

(54) AUTOMATED WORK CHART SYSTEMS AND METHODS

(71) Applicant: R4N63R Capital LLC, Wilmington, DE (US)

(72) Inventors: Ananth Uggirala, Mountain View, CA (US); Yash Raj Chhabra, New Delhi (IN); Zakaria Ibrahim Assoul, Oakland, CA (US); Krishnendu Chaudhury, Saratoga, CA (US); Prasad Narasimha Akella, Palo Alto, CA (US)

(73) Assignee: R4N63R CAPITAL LLC, Wilmington, DE (US)

( * ) Notice: Subject to any disclaimer, the term of this patent is extended or adjusted under 35 U.S.C. 154(b) by 252 days.

This patent is subject to a terminal disclaimer.

(21) Appl. No.: 16/181,173

(22) Filed: Nov. 5, 2018

(65) Prior Publication Data

US 2019/0138971 A1 May 9, 2019

Related U.S. Application Data

(60) Provisional application No. 62/581,541, filed on Nov. 3, 2017.

(51) Int. Cl.
*G05B 19/418* (2006.01)
*G06F 9/448* (2018.01)
(Continued)

(52) U.S. Cl.
CPC ... *G05B 19/4183* (2013.01); *G05B 19/41835* (2013.01); *G06F 9/4498* (2018.02);
(Continued)

(58) Field of Classification Search
CPC .. G06K 9/00335; G06K 9/6262; G06N 20/00; G06N 3/008; G06N 3/006;
(Continued)

(56) References Cited

U.S. PATENT DOCUMENTS 6,963,827 B1 * 11/2005 Elyea ................ G09B 23/28
382/128
7,401,728 B2 7/2008 Markham et al.
(Continued)

FOREIGN PATENT DOCUMENTS

CN 106094707 A 11/2016
CN 107066979 A 8/2017
(Continued)

OTHER PUBLICATIONS

Sepp Hochreiter & Jurgen Schmidhuber, *Long Short-Term memory*, Neural Computation, vol. 9, Issue 8, p. 1735-1780, Nov. 15, 1997.
(Continued)

*Primary Examiner* — Mehmet Yesildag
*Assistant Examiner* — Ayanna Minor
(74) *Attorney, Agent, or Firm* — Dorsey & Whitney LLP

(57) ABSTRACT

The systems and methods provide an action recognition and analytics tool for use in manufacturing, health care services, shipping, retailing and other similar contexts. Machine learning action recognition can be utilized to determine
(Continued)

cycles, processes, actions, sequences, objects and or the like in one or more sensor streams. The sensor streams can include, but are not limited to, one or more video sensor frames, thermal sensor frames, infrared sensor frames, and or three-dimensional depth frames. The analytics tool can provide for automatic creation of work charts.

19 Claims, 15 Drawing Sheets

(51) Int. Cl.

| | |
|---|---|
| *G06F 9/48* | (2006.01) |
| *G06F 11/07* | (2006.01) |
| *G06F 11/34* | (2006.01) |
| *G06F 16/22* | (2019.01) |
| *G06F 16/23* | (2019.01) |
| *G06F 16/2455* | (2019.01) |
| *G06F 16/901* | (2019.01) |
| *G06F 16/9035* | (2019.01) |
| *G06F 16/904* | (2019.01) |
| *G06F 30/20* | (2020.01) |
| *G06F 30/23* | (2020.01) |
| *G06F 30/27* | (2020.01) |
| *G06N 3/008* | (2023.01) |
| *G06N 3/04* | (2023.01) |
| *G06N 3/044* | (2023.01) |
| *G06N 3/045* | (2023.01) |
| *G06N 3/08* | (2023.01) |
| *G06N 3/084* | (2023.01) |
| *G06N 7/01* | (2023.01) |
| *G06N 20/00* | (2019.01) |
| *G06Q 10/06* | (2023.01) |
| *G06Q 10/0631* | (2023.01) |
| *G06Q 10/0639* | (2023.01) |
| *G06T 19/00* | (2011.01) |
| *G06V 10/25* | (2022.01) |
| *G06V 10/44* | (2022.01) |
| *G06V 10/82* | (2022.01) |
| *G06V 20/52* | (2022.01) |
| *G06V 40/20* | (2022.01) |
| *G09B 19/00* | (2006.01) |
| *B25J 9/16* | (2006.01) |
| *G01M 99/00* | (2011.01) |
| *G05B 19/423* | (2006.01) |
| *G05B 23/02* | (2006.01) |
| *G06F 18/21* | (2023.01) |
| *G06F 111/10* | (2020.01) |
| *G06F 111/20* | (2020.01) |
| *G06N 3/006* | (2023.01) |
| *G06Q 10/083* | (2023.01) |
| *G06Q 50/26* | (2012.01) |
| *G16H 10/60* | (2018.01) |

(52) U.S. Cl.
CPC ........ *G06F 9/4881* (2013.01); *G06F 11/0721* (2013.01); *G06F 11/079* (2013.01); *G06F 11/3452* (2013.01); *G06F 16/2228* (2019.01); *G06F 16/2365* (2019.01); *G06F 16/24568* (2019.01); *G06F 16/9024* (2019.01); *G06F 16/9035* (2019.01); *G06F 16/904* (2019.01); *G06F 30/20* (2020.01); *G06F 30/23* (2020.01); *G06F 30/27* (2020.01); *G06N 3/008* (2013.01); *G06N 3/04* (2013.01); *G06N 3/044* (2023.01); *G06N 3/045* (2023.01); *G06N 3/08* (2013.01); *G06N 3/084* (2013.01); *G06N 7/01* (2023.01); *G06N 20/00* (2019.01); *G06Q 10/06* (2013.01); *G06Q 10/063112* (2013.01); *G06Q 10/06316* (2013.01); *G06Q 10/06393* (2013.01); *G06Q 10/06395* (2013.01); *G06Q 10/06398* (2013.01); *G06T 19/006* (2013.01); *G06V 10/25* (2022.01); *G06V 10/454* (2022.01); *G06V 10/82* (2022.01); *G06V 20/52* (2022.01); *G06V 40/20* (2022.01); *G09B 19/00* (2013.01); *B25J 9/1664* (2013.01); *B25J 9/1697* (2013.01); *G01M 99/005* (2013.01); *G05B 19/41865* (2013.01); *G05B 19/423* (2013.01); *G05B 23/0224* (2013.01); *G05B 2219/32056* (2013.01); *G05B 2219/36442* (2013.01); *G06F 18/217* (2023.01); *G06F 2111/10* (2020.01); *G06F 2111/20* (2020.01); *G06N 3/006* (2013.01); *G06Q 10/083* (2013.01); *G06Q 50/26* (2013.01); *G16H 10/60* (2018.01)

(58) Field of Classification Search
CPC .. G06N 7/005; G05B 19/423; G05B 23/0224; G05B 2219/36442; G05B 2219/32056; G06F 9/4498; G06F 16/24568; G06F 16/904; G06F 16/9035; G06F 16/2228; G06F 16/2365; G06F 16/9024; G06F 9/4881; G06F 11/3452; G06F 2111/20; G06F 211/10; G06Q 10/06; G06Q 10/083; G06Q 50/26; G09B 19/00; G16H 10/60; B25J 9/1697; G01M 99/005; G06T 19/006

See application file for complete search history.

(56) References Cited

U.S. PATENT DOCUMENTS

| | | | |
|---|---|---|---|
| 8,260,783 B2 | 9/2012 | Milam | |
| 8,306,931 B1 | 11/2012 | Bowman et al. | |
| 9,471,610 B1 | 10/2016 | Long et al. | |
| 9,921,726 B1 | 3/2018 | Sculley et al. | |
| 10,445,702 B1* | 10/2019 | Hunt | G06Q 10/1097 |
| 10,713,794 B1* | 7/2020 | He | G06N 3/084 |
| 10,852,712 B2 | 12/2020 | Ben-Bassat et al. | |
| 11,226,720 B1 | 1/2022 | Vandivere et al. | |
| 2003/0229471 A1 | 12/2003 | Guralnik et al. | |
| 2005/0105765 A1 | 5/2005 | Han et al. | |
| 2006/0224254 A1 | 10/2006 | Rumi et al. | |
| 2006/0241792 A1 | 10/2006 | Pretlove et al. | |
| 2006/0271526 A1 | 11/2006 | Charnock et al. | |
| 2009/0016599 A1 | 1/2009 | Eaton et al. | |
| 2009/0016600 A1 | 1/2009 | Eaton et al. | |
| 2009/0089227 A1 | 4/2009 | Sturrock et al. | |
| 2010/0082512 A1 | 4/2010 | Myerson et al. | |
| 2011/0043626 A1 | 2/2011 | Cobb et al. | |
| 2012/0197898 A1 | 8/2012 | Pandey et al. | |
| 2012/0225413 A1 | 9/2012 | Kotranza et al. | |
| 2013/0234854 A1 | 9/2013 | Mukherjee et al. | |
| 2013/0307693 A1 | 11/2013 | Stone et al. | |
| 2013/0339923 A1 | 12/2013 | Xu et al. | |
| 2014/0003710 A1 | 1/2014 | Seow et al. | |
| 2014/0079297 A1 | 3/2014 | Tadayon et al. | |
| 2014/0172357 A1 | 6/2014 | Heinonen | |
| 2014/0222813 A1 | 8/2014 | Yang et al. | |
| 2014/0275888 A1 | 9/2014 | Wegerich et al. | |
| 2014/0277593 A1 | 9/2014 | Nixon et al. | |
| 2014/0279776 A1 | 9/2014 | Brown et al. | |
| 2014/0326084 A1 | 11/2014 | Bhushan | |
| 2014/0337000 A1 | 11/2014 | Asenjo et al. | |
| 2014/0379156 A1 | 12/2014 | Kamel et al. | |
| 2015/0110388 A1 | 4/2015 | Eaton et al. | |
| 2015/0363438 A1 | 12/2015 | Botelho | |
| 2015/0364158 A1 | 12/2015 | Gupte et al. | |
| 2016/0085607 A1 | 3/2016 | Marr et al. | |

(56) References Cited

U.S. PATENT DOCUMENTS

| | | |
|---|---|---|
| 2016/0322078 A1 | 11/2016 | Bose et al. |
| 2016/0375524 A1* | 12/2016 | Hsu .................. B23K 26/03 |
| | | 228/8 |
| 2017/0098161 A1 | 4/2017 | Ellenbogen et al. |
| 2017/0232613 A1 | 8/2017 | Ponulak et al. |
| 2017/0243154 A1 | 8/2017 | Fletter et al. |
| 2017/0262697 A1 | 9/2017 | Kaps et al. |
| 2017/0308800 A1 | 10/2017 | Cichon et al. |
| 2017/0320102 A1 | 11/2017 | McVaugh et al. |
| 2018/0011973 A1 | 1/2018 | Fish et al. |
| 2018/0039745 A1* | 2/2018 | Chevalier .............. G16H 30/20 |
| 2018/0059630 A1 | 3/2018 | Yang et al. |
| 2018/0139309 A1 | 5/2018 | Pasam et al. |
| 2018/0324199 A1 | 11/2018 | Crotinger et al. |
| 2018/0330287 A1* | 11/2018 | Tripathi ................. G06Q 10/06 |
| 2019/0034734 A1* | 1/2019 | Yen ..................... G06F 18/2413 |
| 2019/0138971 A1 | 5/2019 | Uggirala et al. |
| 2019/0320898 A1* | 10/2019 | Dirghangi .............. A61B 3/156 |
| 2020/0051203 A1 | 2/2020 | Nurvitadhi et al. |
| 2020/0293972 A1* | 9/2020 | Arao .................. G06K 9/00335 |

FOREIGN PATENT DOCUMENTS

| | | |
|---|---|---|
| EP | 2626757 | 8/2013 |
| EP | 2626757 A1 | 8/2013 |
| EP | 2996006 A1 | 3/2016 |
| WO | WO2012141601 | 10/2012 |
| WO | WO2017040167 | 3/2017 |
| WO | 2017091883 A1 | 6/2017 |
| WO | 2018009405 A1 | 1/2018 |

OTHER PUBLICATIONS

Matthew Zeiler & Rob Fergus, Visualizing and Understanding Convolution Networks, arXiv;1311.2901v3, Nov. 28, 2013, pp. 11.

Ross Girshick, *Fast R-CNN*, Proceedings of the 2015 IEEE International Conference on Computer Vision (ICCV), p. 1440-1448, Dec. 7-13, 2015.

Shaoqing Ren et al., *Faster R-CNN: Towards Real Time Object Detection with Region Proposal Networks*, Proceedings of the 28th International Conference on Neural Information Processing Systems, vol. 1, p. 91-99, Dec. 7-12, 2015.

Christian Szegedy et al., *Inception-v4, Inception-Resnet and the Impact of Residual Connections on Learning*, ICLR 2016 Workshop, Feb. 18, 2016.

Jonathan Huang et al., *Speed/Accuracy Trade-Offs for Modern Convolutional Object Detectors*, Proceedings of the 2017 IEEE Conference on Computer Vision and Pattern Recognition (CVPR), Nov. 9, 2017.

Chen, L., et al., "Sensor-Based Activity Recognition", in IEEE Transactions on Systems, Man, and Cybernetics, Part C (Applications and Reviews), vol. 42, No. 6, doi: 10.1109/TSMCC.2012.2198883, Nov. 2012, pp. 790-808.

Ko, T., "A Survey on Behavior Analysis in Video Surveillance for Homeland Security Applications", 2008 37th IEEE Applied Imagery Pattern Recognition Workshop, Washington, DC, USA, doi: 10.1109/AIPR.2008/4906450, 2008, pp. 1-8.

Damiao, Alexandre, "Convolution of images", retrieved from https://www.youtube.com/watch?v=YgtModJ-4cw, 2018 (Year: 2018).

Xie, Saining, et al., "Rethinking spatiotemporal feature learning for video understanding", arXiv preprint arXiv: 1712.04851 1.2 (2017): 5. (Year: 2017).

\* cited by examiner

AUTOMATED WORK CHART SYSTEMS AND METHODS

CROSS-REFERENCE TO RELATED APPLICATIONS

This application claims the benefit of U.S. Provisional Patent Application No. 62/581,541 filed Nov. 3, 2017, which is incorporated herein in its entirety.

BACKGROUND OF THE INVENTION

As the world's population continues to grow, the demand for goods and services continues to increase. Industries grow in lockstep with the increased demand and often require an ever-expanding network of enterprises employing various processes to accommodate the growing demand for goods and services. For example, an increased demand in automobiles can increase the need for robust assembly lines, capable of completing a larger number of processes in each station on the assembly line while minimizing anomalies and reducing completion times associate with each process. Typically, process anomalies are the result of an operator deviating from or incorrectly performing one or more actions. In addition, variances in the completion times of a process can be attributed to inadequate designs that result in an operator being challenged to execute the required actions in the required time. Quite often, if the number of actions per station increases either due to an increase in the complexity of the actions or a decrease in the time available in each station, the cognitive load on the operator increases, resulting in higher deviation rates.

Common quality improvement and process optimization methodologies, for use by manufacturing organizations, include Toyota's Toyota Production System and Motorola's Six-Sigma. The optimization methodologies such as Lean Manufacturing and Six-Sigma rely on manual techniques to gather data on human activity. The data gathered using such manual techniques typically represent a small and incomplete data set. Worse, manual techniques can generate fundamentally biased data sets, since the persons being measured may be "performing" for the observer and not providing truly representative samples of their work, which is commonly referred to as the Hawthorne and Heisenberg effect. Such manual techniques can also be subject to substantial delays between the collection and analysis of the data.

There is currently a growth in the use of Industrial Internet of Things (IIoT) devices in manufacturing and other contexts. However, machines currently only perform a small portion of tasks in manufacturing. Therefore, instrumenting machines used in manufacturing with electronics, software, sensors, actuators and connectivity to collect, exchange and utilize data is centered on a small portion of manufacturing tasks, which the Boston Consulting Group estimated in 2016 to be about 10% of the task or action that manufactures use to build products. Accordingly, IIoT devices also provides an incomplete data set.

Accordingly, there is a continuing need for systems and methods for collecting information about manufacturing, health care services, shipping, retailing and other similar context and providing analytic tools for improving the performance in such contexts. Amongst other reasons, the information could for example be utilized to improve the quality of products or services being delivered, for training employees, for communicating with customers and handling warranty claims and recalls.

SUMMARY OF THE INVENTION

The present technology may best be understood by referring to the following description and accompanying drawings that are used to illustrate embodiments of the present technology directed toward automated work charting.

In aspects, an action recognition and analytics system can be utilized to determine cycles, processes, actions, sequences, objects and or the like in one or more sensor streams. The sensor streams can include, but are not limited to, one or more frames of video sensor data, thermal sensor data, infrared sensor data, and or three-dimensional depth sensor data. The action recognition and analytics system can be applied to any number of contexts, including but not limited to manufacturing, health care services, shipping and retailing. The sensor streams, and the determined cycles, processes, actions, sequences, objects, parameters and or the like can be stored in a data structure. The determined cycles, processes, actions, sequences objects and or the like can be indexed to corresponding portions of the sensor streams. The action recognition and analytics system can provide for automated work charting.

In one embodiment, a work charting method can include receiving one or more given indicators or criteria. One or more given data sets can be accessed based on the one or more given indicators or criteria. The one or more given data sets can include one or more indicators of at least one of one or more cycles, one or more processes, one or more actions, one or more sequences, one or more objects, and one or more parameters indexed to corresponding portions of the one or more sensor streams. A representative data set can be determined from the one or more given data sets. A work chart can be created from the representative data set. The work chart can include a plurality of work elements and dependencies between the work elements.

In another embodiment, an action recognition and analytics system can include one or more data storage units, one or more interfaces, and one or more engines. The one or more engines can be configured to receive one or more given indicators or criteria. The one or more engines can also be configured to access one or more given data sets stored on the one or more data storage units based on the one or more given indicators or criteria. The one or more given data sets can include one or more indicators of at least one of one or more cycles, one or more processes, one or more actions, one or more sequences, one or more objects, and one or more parameters, indexed to corresponding portions of one or more sensor streams. The one or more engines can be configured to determine a representative data set from the one or more given data sets. The one or more engines can be configured to create a work chart from the representative data set, wherein the work chart include a plurality of work elements and dependencies between the work elements.

The one or more analytics front-end units can be configured to receiving a unique identifier of a given instance of the subject. The one or more analytics front-end units can be configured to access the one or more data structures on the one or more data storage devices including a plurality of data sets mapped to a plurality of unique identifiers to retrieve indicators of one or more cycles, processes, actions, sequences, objects, and parameters indexed to corresponding portions of the sensor streams for the given instance of the subject. The one or more analytics front-end units can also be configured to access the one or more data structures on the data storage unit including the sensor streams to retrieve corresponding portions of the sensor streams indexed by the one or more cycles, processes, actions, sequences, objects, and parameters for the given instance of the subject. The analytics front-end unit can be configured to output the corresponding portions of the sensor streams and the corresponding one or more cycles, processes, actions, sequences, objects, parameters for the given instance of the subject.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Embodiments of the present technology are illustrated by way of example and not by way of limitation, in the figures of the accompanying drawings and in which like reference numerals refer to similar elements and in which.

DETAILED DESCRIPTION OF THE INVENTION

Figure 1:
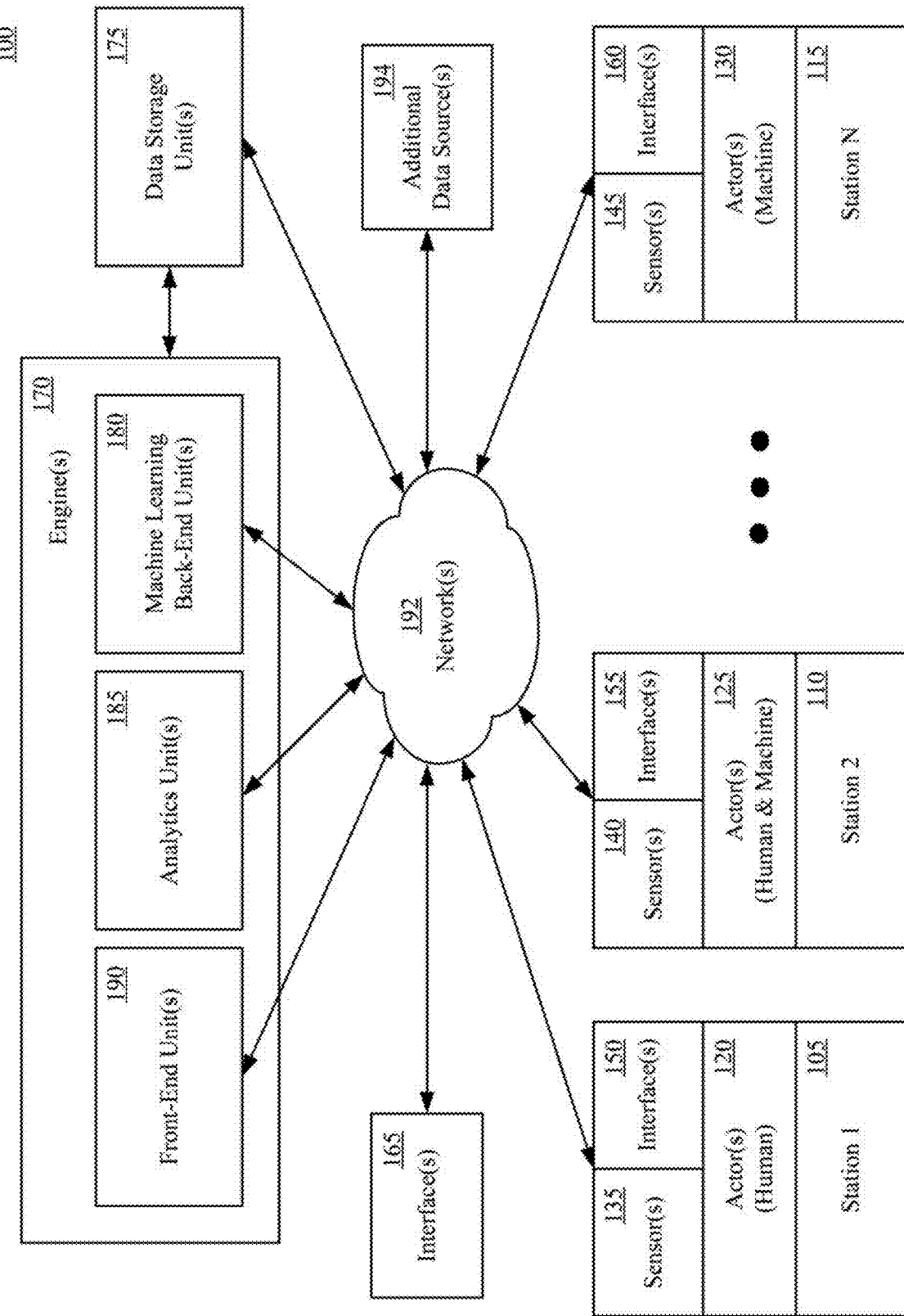
FIG. 1 shows an action recognition and analytics system, in accordance with aspect of the present technology.

Reference will now be made in detail to the embodiments of the present technology, examples of which are illustrated in the accompanying drawings. While the present technology will be described in conjunction with these embodiments, it will be understood that they are not intended to limit the invention to these embodiments. On the contrary, the invention is intended to cover alternatives, modifications and equivalents, which may be included within the scope of the invention as defined by the appended claims. Furthermore, in the following detailed description of the present technology, numerous specific details are set forth in order to provide a thorough understanding of the present technology. However, it is understood that the present technology may be practiced without these specific details. In other instances, well-known methods, procedures, components, and circuits have not been described in detail as not to unnecessarily obscure aspects of the present technology.

Some embodiments of the present technology which follow are presented in terms of routines, modules, logic blocks, and other symbolic representations of operations on data within one or more electronic devices. The descriptions and representations are the means used by those skilled in the art to most effectively convey the substance of their work to others skilled in the art. A routine, module, logic block and/or the like, is herein, and generally, conceived to be a self-consistent sequence of processes or instructions leading to a desired result. The processes are those including physical manipulations of physical quantities. Usually, though not necessarily, these physical manipulations take the form of electric or magnetic signals capable of being stored, transferred, compared and otherwise manipulated in an electronic device. For reasons of convenience, and with reference to common usage, these signals are referred to as data, bits, values, elements, symbols, characters, terms, numbers, strings, and/or the like with reference to embodiments of the present technology.

It should be borne in mind, however, that all of these terms are to be interpreted as referencing physical manipulations and quantities and are merely convenient labels and are to be interpreted further in view of terms commonly used in the art. Unless specifically stated otherwise as apparent from the following discussion, it is understood that through discussions of the present technology, discussions utilizing the terms such as "receiving," and/or the like, refer to the actions and processes of an electronic device such as an electronic computing device that manipulates and transforms data. The data is represented as physical (e.g., electronic) quantities within the electronic device's logic circuits, registers, memories and/or the like, and is transformed into other data similarly represented as physical quantities within the electronic device.

As used herein, the use of the disjunctive is intended to include the conjunctive. The use of definite or indefinite articles is not intended to indicate cardinality. In particular, a reference to "the" object or "a" object is intended to denote also one of a possible plurality of such objects. It is also to be understood that the phraseology and terminology used herein is for the purpose of description and should not be regarded as limiting.

As used herein the term process can include processes, procedures, transactions, routines, practices, and the like. As used herein, the term sequence can include sequences, orders, arrangements, and the like. As used herein the term action can include actions, steps, tasks, activity, motion, movement, and the like. As used herein the term object can include objects, parts, components, items, elements, pieces, assemblies, sub-assemblies, and the like. As used herein a process can include a set of actions or one or more subsets of actions, arranged in one or more sequences, and performed on one or more objects by one or more actors. As used herein a cycle can include a set of processes or one or more subsets of processes performed in one or more sequences. As used herein a sensor stream can include a video sensor stream, thermal sensor stream, infrared sensor stream, hyperspectral sensor stream, audio sensor stream, depth data stream, and the like. As used herein frame based sensor stream can include any sensor stream that can be represented by a two or more dimensional array of data values. As used herein the term parameter can include parameters, attributes, or the like. As used herein the term indicator can include indicators, identifiers, labels, tags, states, attributes, values or the like. As used herein the term feedback can include feedback, commands, directions, alerts, alarms, instructions, orders, and the like. As used herein the term actor can include actors, workers, employees, operators, assemblers, contractors, associates, managers, users, entities, humans, cobots, robots, and the like as well as combinations of them. As used herein the term robot can include a machine, device, apparatus or the like, especially one programmable by a computer, capable of carrying out a series of actions automatically. The actions can be autonomous, semi-autonomous, assisted, or the like. As used herein the term cobot can include a robot intended to interact with humans in a shared workspace. As used herein the term package can include packages, packets, bundles, boxes, containers, cases, cartons, kits, and the like. As used herein, real time can include responses within a given latency, which can vary from sub-second to seconds.

Referring to FIG. 1 an action recognition and analytics system, in accordance with aspect of the present technology, is shown. The action recognition and analytics system 100 can be deployed in a manufacturing, health care, warehousing, shipping, retail, restaurant or similar context. A manufacturing context, for example, can include one or more stations 105-115 and one or more actors 120-130 disposed at the one or more stations. The actors can include humans, machine or any combination therefore. For example, individual or multiple workers can be deployed at one or more stations along a manufacturing assembly line. One or more robots can be deployed at other stations. A combination of one or more workers and/or one or more robots can be deployed additional stations It is to be noted that the one or more stations 105-115 and the one or more actors are not generally considered to be included in the system 100.

In a health care implementation, an operating room can comprise a single station implementation. A plurality of sensors, such as video cameras, thermal imaging sensors, depth sensors, or the like, can be disposed non-intrusively at various positions around the operating room. One or more additional sensors, such as audio, temperature, acceleration, torque, compression, tension, or the like sensors, can also be disposed non-intrusively at various positions around the operating room.

In a shipping implementation, the plurality of stations may represent different loading docks, conveyor belts, forklifts, sorting stations, holding areas, and the like. A plurality of sensors, such as video cameras, thermal imaging sensors, depth sensors, or the like, can be disposed non-intrusively at various positions around the loading docks, conveyor belts, forklifts, sorting stations, holding areas, and the like. One or more additional sensors, such as audio, temperature, acceleration, torque, compression, tension, or the like sensors, can also be disposed non-intrusively at various positions.

In a retailing implementation, the plurality of stations may represent one or more loading docks, one or more stock rooms, the store shelves, the point of sale (e.g. cashier stands, self-checkout stands and auto-payment geofence), and the like. A plurality of sensors such as video cameras, thermal imaging sensors, depth sensors, or the like, can be disposed non-intrusively at various positions around the loading docks, stock rooms, store shelves, point of sale stands and the like. One or more additional sensors, such as audio, acceleration, torque, compression, tension, or the like sensors, can also be disposed non-intrusively at various positions around the loading docks, stock rooms, store shelves, point of sale stands and the like.

In a warehousing or online retailing implementation, the plurality of stations may represent receiving areas, inventory storage, picking totes, conveyors, packing areas, shipping areas, and the like. A plurality of sensors, such as video cameras, thermal imaging sensors, depth sensors, or the like, can be disposed non-intrusively at various positions around the receiving areas, inventory storage, picking totes, conveyors, packing areas, and shipping areas. One or more additional sensors, such as audio, temperature, acceleration, torque, compression, tension, or the like sensors, can also be disposed non-intrusively at various positions.

Aspect of the present technology will be herein further described with reference to a manufacturing context so as to best explain the principles of the present technology without obscuring aspects of the present technology. However, the present technology as further described below can also be readily applied in health care, warehousing, shipping, retail, restaurants, and numerous other similar contexts.

The action recognition and analytics system 100 can include one or more interfaces 135-165. The one or more interface 135-165 can include one or more sensors 135-145 disposed at the one or more stations 105-115 and configured to capture streams of data concerning cycles, processes, actions, sequences, object, parameters and or the like by the one or more actors 120-130 and or at the station 105-115. The one or more sensors 135-145 can be disposed non-intrusively, so that minimal to changes to the layout of the assembly line or the plant are required, at various positions around one or more of the stations 105-115. The same set of one or more sensors 135-145 can be disposed at each station 105-115, or different sets of one or more sensors 135-145 can be disposed at different stations 105-115. The sensors 135-145 can include one or more sensors such as video cameras, thermal imaging sensors, depth sensors, or the like. The one or more sensors 135-145 can also include one or more other sensors, such as audio, temperature, acceleration, torque, compression, tension, or the like sensors.

The one or more interfaces 135-165 can also include but not limited to one or more displays, touch screens, touch pads, keyboards, pointing devices, button, switches, control panels, actuators, indicator lights, speakers, Augmented Reality (AR) interfaces, Virtual Reality (VR) interfaces, desktop Personal Computers (PCs), laptop PCs, tablet PCs, smart phones, robot interfaces, cobot interfaces. The one or more interfaces 135-165 can be configured to receive inputs from one or more actors 120-130, one or more engines 170 or other entities. Similarly, the one or more interfaces 135-165 can be configured to output to one or more actors 120-130, one or more engine 170 or other entities. For example, the one or more front-end units 190 can output one or more graphical user interfaces to present training content, work charts, real time alerts, feedback and or the like on one or more interfaces 165, such displays at one or more stations 105-115, at management portals on tablet PCs, administrator portals as desktop PCs or the like. In another example, the one or more front-end units 190 can control an actuator to push a defective unit of the assembly line when a defect is detected. The one or more front-end units can also receive responses on a touch screen display device, keyboard, one or more buttons, microphone or the like from one or more actors. Accordingly, the interfaces 135-165 can implement an analysis interface, mentoring interface and or the like of the one or more front-end units 190.

The action recognition and analytics system 100 can also include one or more engines 170 and one or more data storage units 175. The one or more interfaces 135-165, the one or more data storage units 175, the one or more machine learning back-end units 180, the one or more analytics units 185, and the one or more front-end units 190 can be coupled together by one or more networks 192. It is also to be noted that although the above described elements are described as separate elements, one or more elements of the action recognition and analytics system 100 can be combined together or further broken into different elements.

The one or more engines 170 can include one or more machine learning back-end units 180, one or more analytics units 185, and one or more front-end units 190. The one or more data storage units 175, the one or more machine learning back-end units 180, the one or more analytics units 185, and the one or more analytics front-end units 190 can be implemented on a single computing device, a common set of computing devices, separate computing device, or different sets of computing devices that can be distributed across the globe inside and outside an enterprise. Aspects of the one or more machine learning back-end units 180, the one or more analytics units 185 and the one or more front-end units 190, and or other computing units of the action recognition and analytics system 100 can be implemented by one or more central processing units (CPU), one or more graphics processing units (GPU), one or more tensor processing units (TPU), one or more digital signal processors (DSP), one or more microcontrollers, one or more field programmable gate arrays and or the like, and any combination thereof. In addition, the one or more data storage units 175, the one or more machine learning back-end units 180, the one or more analytics units 185, and the one or more front-end units 190 can be implemented locally to the one or more stations 105-115, remotely from the one or more stations 105-115, or any combination of locally and remotely. In one example, the one or more data storage units 175, the one or more machine learning back-end units 180, the one or more analytics units 185, and the one or more front-end units 190 can be implemented on a server local (e.g., on site at the manufacturer) to the one or more stations 105-115. In another example, the one or more machine learning back-end units 180, the one or more storage units 175 and analytics front-end units 190 can be implemented on a cloud computing service remote from the one or more stations 105-115. In yet another example, the one or more data storage units 175 and the one or more machine learning back-end units 180 can be implemented remotely on a server of a vendor, and one or more data storage units 175 and the one or more front-end units 190 are implemented locally on a server or computer of the manufacturer. In other examples, the one or more sensors 135-145, the one or more machine learning back-end units 180, the one or more front-end unit 190, and other computing units of the action recognition and analytics system 100 can perform processing at the edge of the network 192 in an edge computing implementation. The above example of the deployment of one or more computing devices to implement the one or more interfaces 135-165, the one or more engines 170, the one or more data storage units 175 and one or more analytics front-end units 190, are just some of the many different configuration for implementing the one or more machine learning back-end units 180, one or more data storage units 175. Any number of computing devices, deployed locally, remotely, at the edge or the like can be utilized for implementing the one or more machine learning back-end units 180, the one or more data storage units 175, the one or more analytics front-end units 190 or other computing units.

The action recognition and analytics system 100 can also optionally include one or more data compression units associated with one or more of the interfaces 135-165. The data compression units can be configured to compress or decompress data transmitted between the one or more interface 135-165, and the one or more engines 170. Data compression, for example, can advantageously allow the sensor data from the one or more interface 135-165 to be transmitted across one or more existing networks 192 of a manufacturer. The data compression units can also be integral to one or more interfaces 135-165 or implemented separately. For example, video capture sensors may include an integral Motion Picture Expert Group (MPEG) compression unit, (e.g., H-264 encoder/decoder). In an exemplary implementation, the one or more data compression units can use differential coding and arithmetic encoding to obtain a 20× reduction in the size of depth data from depth sensors. The data from a video capture sensor can comprise roughly 30 GB of H.264 compressed data per camera, per day for a factory operation with three eight-hour shifts. The depth data can comprise roughly another 400 GB of uncompressed data per sensor, per day. The depth data can be compressed by an algorithm to approximately 20 GB per sensor, per day. Together, a set of a video sensor and a depth sensor can generate approximately 50 GB of compressed data per day. The compression can allow the action recognition and analytics system 100 to use a factory's network 192 to move and store data locally or remotely (e.g., cloud storage).

The action recognition and analytics system 100 can also be communicatively coupled to additional data sources 194, such as but not limited to a Manufacturing Execution Systems (MES), warehouse management system, or patient management system. The action recognition and analytics system 100 can receive additional data, including one or more additional sensor streams, from the additional data sources 194. The action recognition and analytics system 100 can also output data, sensor streams, analytics result and or the like to the additional data sources 194. For example, the action recognition can identify a barcode on an object and provide the barcode input to a MES for tracking.

The action recognition and analytics system 100 can continually measure aspects of the real-world, making it possible to describe a context utilizing vastly more detailed data sets, and to solve important business problems like line balancing, ergonomics, and or the like. The data can also reflect variations over time. The one or more machine learning back-end units 170 can be configured to recognize, in real time, one or more cycles, processes, actions, sequences, objects, parameters and the like in the sensor streams received from the plurality of sensors 135-145. The one or more machine learning back-end units 180 can recognize cycles, processes, actions, sequences, objects, parameters and the like in sensor streams utilizing deep learning, decision tree learning, inductive logic programming, clustering, reinforcement learning, Bayesian networks, and or the like.

Figure 2:
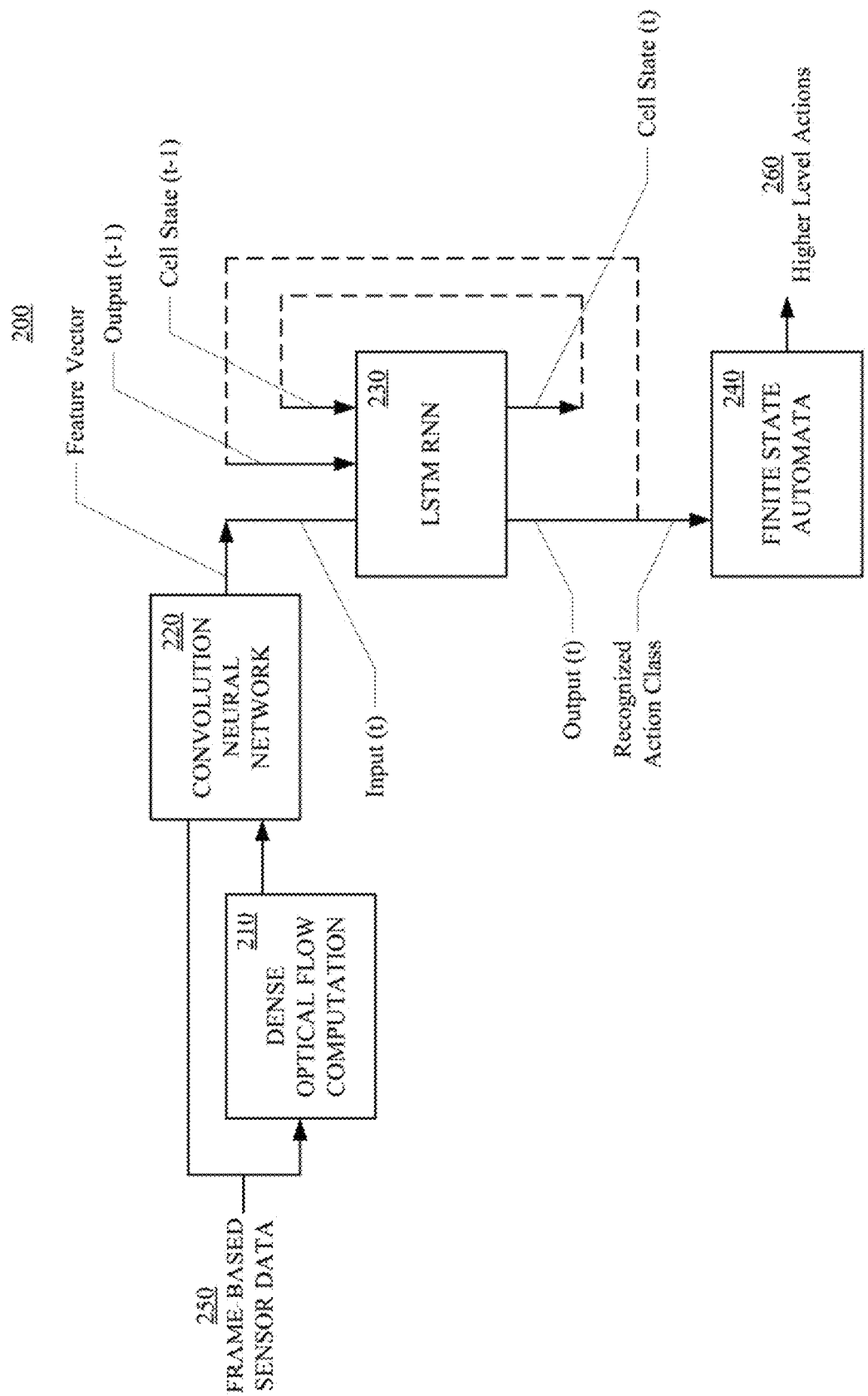
FIG. 2 shows an exemplary deep learning type machine learning back-end unit, in accordance with aspects of the present technology.

Referring now to FIG. 2, an exemplary deep learning type machine learning back-end unit, in accordance with aspects of the present technology, is shown. The deep learning unit 200 can be configured to recognize, in real time, one or more cycles, processes, actions, sequences, objects, parameters and the like in the sensor streams received from the plurality of sensors 135-145. The deep learning unit 200 can include a dense optical flow computation unit 210, a Convolution Neural Networks (CNNs) 220, a Long Short Term Memory (LSTM) Recurrent Neural Network (RNN) 230, and a Finite State Automata (FSA) 240. The CNNs 220 can be based on two-dimensional (2D) or three-dimensional (3D) convolutions. The dense optical flow computation unit 210 can be configured to receive a stream of frame-based sensor data 250 from sensors 135-145. The dense optical flow computation unit 210 can be configured to estimate an optical flow, which is a two-dimension (2D) vector field where each vector is a displacement vector showing the movement of points from a first frame to a second frame. The CNNs 220 can receive the stream of frame-based sensor data 250 and the optical flow estimated by the dense optical flow computation unit 210. The CNNs 220 can be applied to video frames to create a digest of the frames. The digest of the frames can also be referred to as the embedding vector. The digest retains those aspects of the frame that help in identifying actions, such as the core visual clues that are common to instances of the action in question.

In a three-dimensional Convolution Neural Network (3D CNN) based approach, spatio-temporal convolutions can be performed to digest multiple video frames together to recognize actions. For 3D CNN, the first two dimension can be along space, and in particular the width and height of each video frame. The third dimension can be along time. The neural network can learn to recognize actions not just from the spatial pattern in individual frame, but also jointly in space and time. The neural network is not just using color patterns in one frame to recognize actions. Instead, the neural network is using how the pattern shifts with time (i.e., motion cues) to come up with its classification. According the 3D CNN is attention driven, in that it proceeds by identifying 3D spatio-temporal bounding boxes as Regions of Interest (RoI) and focusses on them to classify actions.

In one implementation, the input to the deep learning unit 200 can include multiple data streams. In one instance, a video sensor signal, which includes red, green and blue data streams, can comprise three channels. Depth image data can comprise another channel. Additional channels can accrue from temperature, sound, vibration, data from sensors (e.g., torque from a screwdriver) and the like. From the RGB and depth streams, dense optical flow fields can be computed by the dense optical flow computation unit 210 and fed to the Convolution Neural Networks (CNNs) 220. The RGB and depth streams can also be fed to the CNNs 220 as additional streams of derived data.

The Long Short Term Memory (LSTM) Recurrent Neural Network (RNN) 230 can be fed the digests from the output of the Convolution Neural Networks (CNNs) 220. The LSTM can essentially be a sequence identifier that is trained to recognize temporal sequences of sub-events that constitute an action. The combination of the CNNs and LSTM can be jointly trained, with full back-propagation, to recognize low-level actions. The low-level actions can be referred to as atomic actions, like picking a screw, picking a screwdriver, attaching screw to screwdriver and the like. The Finite State Automata (FSA) 240 can be mathematical models of computations that include a set of state and a set of rules that govern the transition between the states based on the provided input. The FSA 240 can be configured to recognize higher-level actions 260 from the atomic actions. The high-level actions 260 can be referred to as molecular actions, for example turning a screw to affix a hard drive to a computer chassis. The CNNs and LSTM can be configured to perform supervised training on the data from the multiple sensor streams. In one implementation, approximately 12 hours of data, collected over the course of several days, can be utilized to train the CNNs and LSTM combination.

Figure 3:
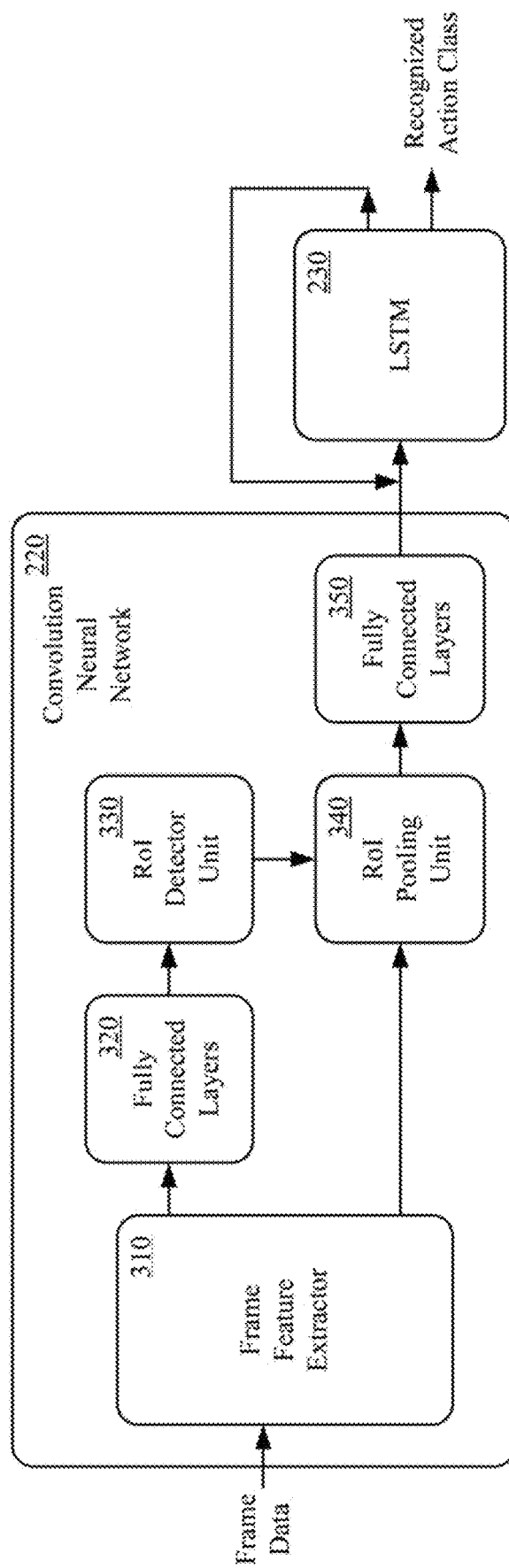
FIG. 3 shows an exemplary Convolution Neural Network (CNN) and Long Short Term Memory (LSTM) Recurrent Neural Network (RNN), in accordance with aspects of the present technology.
Figure 4:
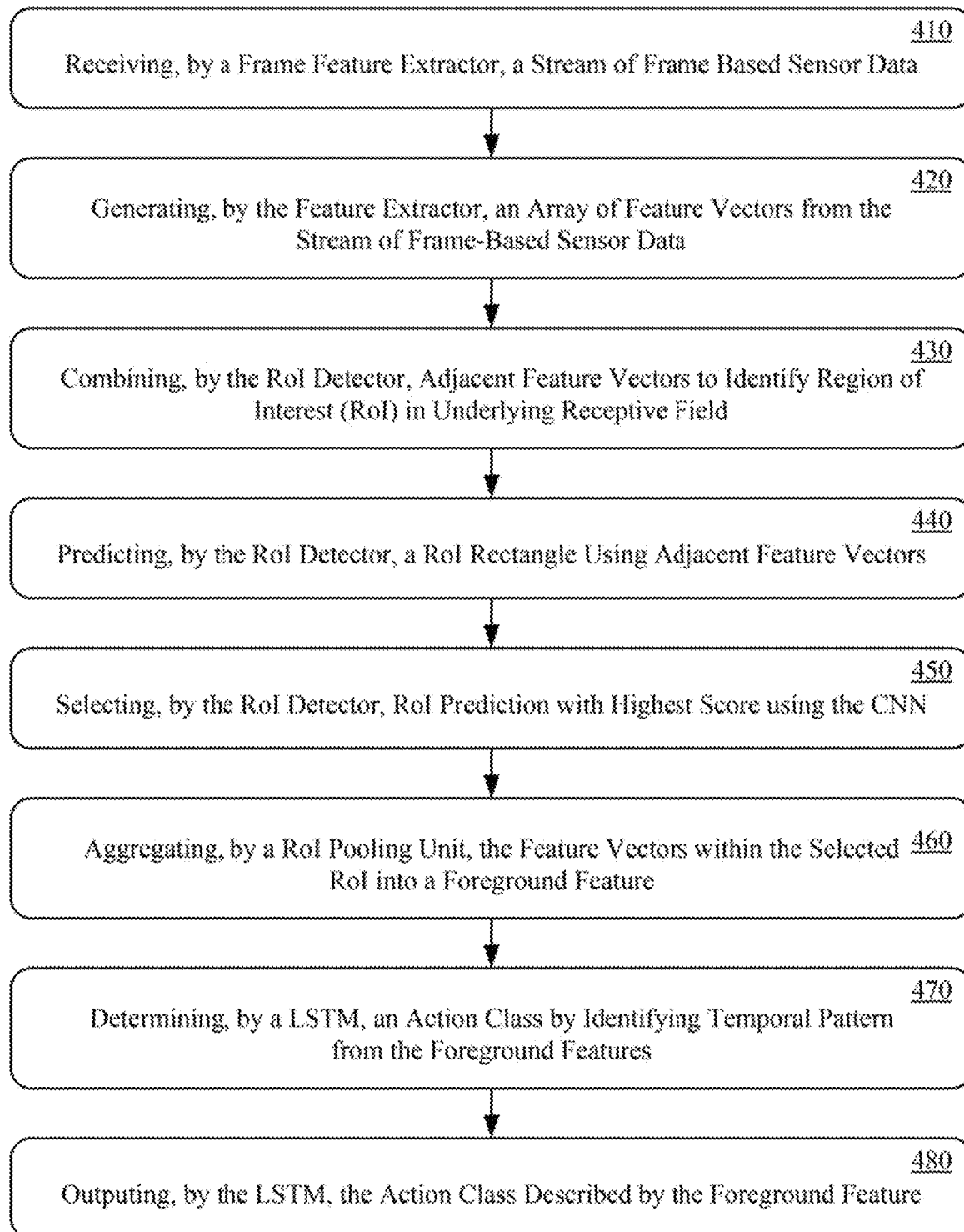
FIG. 4 shows an exemplary method of detecting actions in a sensor stream, in accordance with aspects of the present technology.

Referring now to FIG. 3, an exemplary Convolution Neural Networks (CNNs) and Long Short Term Memory (LSTM) Recurrent Neural Network (RNN), in accordance with aspects of the present technology, is shown. The CNNs can include a frame feature extractor 310, a first Fully Connected (FC) layer 320, a Region of Interest (RoI) detector unit 330, a RoI pooling unit 340, and a second Fully Connected (FC) layer 350. The operation of the CNNs and LSTM will be further explained with reference to FIG. 4, which shows an exemplary method of detecting actions in a sensor stream.

The frame feature extractor 310 of the Convolution Neural Networks (CNNs) 220 can receive a stream of frame-based sensor data, at 410. At 420, the frame feature extractor 310 can perform a two-dimensional convolution operation on the received video frame and generate a two-dimensional array of feature vectors. The frame feature extractor 310 can work on the full resolution image, wherein a deep network is effectively sliding across the image generating a feature vector at each stride position. Thus, each element of the 2D feature vector array is a descriptor for the corresponding receptive field (e.g., fixed portion of the underlying image). The first Fully Connected (FC) layer can flatten the high-level features extracted by the frame feature extractor 310, and provide additional non-linearity and expressive power, enabling the machine to learn complex non-linear combinations of these features.

At 430, the RoI detector unit 330 can combine neighboring feature vectors to make a decision on whether the underlying receptive field belongs to a Region of Interest (RoI) or not. If the underlying receptive field belongs to a RoI, a RoI rectangle can be predicted from the same set of neighboring feature vectors, at 440. At, 450, a RoI rectangle with a highest score can be chosen by the RoI detector unit 330. For the chosen RoI rectangle, the feature vectors lying within it can be aggregated by the RoI pooling unit 340, at 460. The aggregated feature vector is a digest/descriptor for the foreground for that video frame.

In one implementation, the RoI detector unit 330 can determine a static RoI. The static RoI identifies a Region of Interest (RoI) within an aggregate set of feature vectors describing a video frame, and generates a RoI area for the identified RoI. A RoI area within a video frame can be indicated with an RoI rectangle that encompasses an area of the video frame designated for action recognition, such as an area in which actions are performed in a process. Alternatively, the RoI area can be designated with a box, circle, highlighted screen, or any other geometric shape or indicator having various scales and aspect ratios used to encompass a RoI. The area within the RoI rectangle is the area within the video frame to be processed by the Long Short Term Memory (LSTM) for action recognition.

The Long Short Term Memory (LSTM) can be trained using a RoI rectangle that provides, both, adequate spatial context within the video frame to recognize actions and independence from irrelevant portions of the video frame in the background. The trade-off between spatial context and background independence ensures that the static RoI detector can provide clues for the action recognition while avoiding spurious unreliable signals within a given video frame.

In another implementation, the RoI detector unit 330 can determine a dynamic RoI. A RoI rectangle can encompass areas within a video frame in which an action is occurring. By focusing on areas in which action occurs, the dynamic RoI detector enables recognition of actions outside of a static RoI rectangle while relying on a smaller spatial context, or local context, than that used to recognize actions in a static RoI rectangle.

In one implementation, the RoI pooling unit 340 extracts a fixed-sized feature vector from the area within an identified RoI rectangle, and discards the remaining feature vectors of the input video frame. The fixed-sized feature vector, or foreground feature, includes the feature vectors generated by the video frame feature extractor that are located within the coordinates indicating a RoI rectangle as determined by the RoI detector unit 330. Because the RoI pooling unit 340 discards feature vectors not included within the RoI rectangle, the Convolution Neural Networks (CNNs) 220 analyzes actions within the RoI only, thus ensuring that unexpected changes in the background of a video frame are not erroneously analyzed for action recognition.

In one implementation, the Convolution Neural Networks (CNNs) 220 can be an Inception ResNet. The Inception ResNet can utilize a sliding window style operation. Successive convolution layers output a feature vector at each point of a two-dimensional grid. The feature vector at location (x,y) at level l can be derived by weighted averaging features from a small local neighborhood (aka receptive field) N around the (x,y) at level l-1 followed by a pointwise non-linear operator. The non-linear operator can be the RELU (max(0,x)) operator.

In the sliding window, there can be many more than 7×7 points at the output of the last convolution layer. A Fully Connected (FC) convolution can be taken over the feature vectors from the 7×7 neighborhoods, which is nothing but applying one more convolution. The corresponding output represents the Convolution Neural Networks (CNNs) output at the matching 224×224 receptive field on the input image. This is fundamentally equivalent to applying the CNNs to each sliding window stop. However, no computation is repeated, thus keeping the inferencing computation cost real time on Graphics Processing Unit (GPU) based machines.

The convolution layers can be shared between RoI detector 330 and the video frame feature extractor 310. The RoI detector unit 330 can identify the class independent rectangular region of interest from the video frame. The video frame feature extractor can digest the video frame into feature vectors. The sharing of the convolution layers improves efficiency, wherein these expensive layers can be run once per frame and the results saved and reused.

One of the outputs of the Convolution Neural Networks (CNNs) is the static rectangular Region of Interest (RoI). The term "static" as used herein denotes that the RoI does not vary greatly from frame to frame, except when a scene change occurs, and it is also independent of the output class.

A set of concentric anchor boxes can be employed at each sliding window stop. In one implementation, there can be nine anchor boxes per sliding window stop for combinations of 3 scales and 3 aspect ratios. Therefore, at each sliding window stop there are two set of outputs. The first set of outputs can be a Region of Interest (RoI) present/absent that includes 18 outputs of the form 0 or 1. An output of 0 indicates the absence of a RoI within the anchor box, and an output of 1 indicates the presence of a RoI within the anchor box. The second set of outputs can include Bounding Box (BBox) coordinates including 36 floating point outputs indicating the actual BBox for each of the 9 anchor boxes. The BBox coordinates are to be ignored if the RoI present/absent output indicates the absence of a RoI.

For training, sets of video frames with a per-frame Region of Interest (RoI) rectangle are presented to the network. In frames without a RoI rectangle, a dummy 0×0 rectangle can be presented. The Ground Truth for individual anchor boxes can be created via the Intersection over Union (IoU) of rectangles. For the $i_{th}$ anchor box $\vec{b_i}=\{x_i, y_i, w_i, h_i\}$ the derived Ground Truth for the RoI presence probability can be determined by Equation 1:

$$p_i^* = \begin{cases} 1 & IoU(\vec{b_i}, \vec{g}) >= 0.7 \\ 0 & IoU(\vec{b_i}, \vec{g}) <= 0.1 \\ \text{box unused for training} \end{cases}$$

where $\vec{g}=\{x_g, y_g, w_g, h_g\}$ is the Ground Truth RoI box for the entire frame.

The loss function can be determined by Equation 2:

$$L(p_i, p_i^*, \vec{b_i}, \vec{g}) = \sum_i -p_i^* \log p_i (S(x_i - x_g) + S(y_i - y_g) + S(w_i - w_g) + S(h_i - h_g))$$

where $p_i$ is the predicted probability for presence of Region of Interest (RoI) in the $i_{th}$ anchor box and the smooth loss function can be defined by Equation 3:

$$S(x) = \begin{cases} 0.5x^2 & |x| < 1 \\ |x| - 0.5 & \text{otherwise} \end{cases}$$

The left term in the loss function is the error in predicting the probability of the presence of a RoI, while the second term is the mismatch in the predicted Bounding Box (BBox). It should be noted that the second term vanishes when the ground truth indicates that there is no RoI in the anchor box.

The static Region of Interest (RoI) is independent of the action class. In another implementation, a dynamic Region of Interest (RoI), that is class dependent, is proposed by the CNNs. This takes the form of a rectangle enclosing the part of the image where the specific action is occurring. This increases the focus of the network and takes it a step closer to a local context-based action recognition.

Once a Region of Interest (RoI) has been identified, the frame feature can be extracted from within the RoI. These will yield a background independent frame digest. But this feature vector also needs to be a fixed size so that it can be fed into the Long Short Term Memory (LSTM). The fixed size can be achieved via RoI pooling. For RoI pooling, the RoI can be tiled up into 7×7 boxes. The mean of all feature vectors within a tile can then be determined. Thus, 49 feature vectors that are concatenated from the frame digest can be produced. The second Fully Connected (FC) layer 350 can provide additional non-linearity and expressive power to the machine, creating a fixed size frame digest that can be consumed by the LSTM 230.

At 470, successive foreground features can be fed into the Long Short Term Memory (LSTM) 230 to learn the temporal pattern. The LSTM 230 can be configured to recognize patterns in an input sequence. In video action recognition, there could be patterns within sequences of frames belonging to a single action, referred to as intra action patterns. There could also be patterns within sequences of actions, referred to as inter action patterns. The LSTM can be configured to learn both of these patterns, jointly referred to as temporal patterns. The Long Short Term Memory (LSTM) analyzes a series of foreground features to recognize actions belonging to an overall sequence. In one implementation, the LSTM outputs an action class describing a recognized action associated with an overall process for each input it receives, at 480. In another implementation, each class action is comprised of sets of actions describing actions associated with completing an overall process. Each action within the set of actions can be assigned a score indicating a likelihood that the action matches the action captured in the input video frame. Each action may be assigned a score such that the action with the highest score is designated the recognized action class.

Foreground features from successive frames can be feed into the Long Short Term Memory (LSTM). The foreground feature refers to the aggregated feature vectors from within the Region of Interest (RoI) rectangles. The output of the LSTM at each time step is the recognized action class. The loss for each individual frame is the cross entropy softmax loss over the set of possible action classes. A batch is defined as a set of three randomly selected set of twelve frame sequences in the video stream. The loss for a batch is defined as the frame loss averaged over the frame in the batch. The numbers twelve and three are chose empirically. The overall LSTM loss function is given by Equation 4:

$$L(B, \{S_1, S_2, \ldots, S_{\|B\|}\}) = \sum_{k=1}^{\|B\|} \sum_{t=1}^{\|S_k\|} \sum_{i=1}^{\|A\|} -\left(\frac{e^{a_{t_i}}}{\sum_{j=1}^{\|A\|} e^{a_{t_{ij}}}}\right) \log a_{t_i}^*$$

where B denotes a batch of $\|B\|$ frame sequences $\{S_1, S_2, \ldots, S_{\|B\|}\}$. $S_k$ comprises a sequence $\|S_k\|$ frames, wherein in the present implementation $\|B\|=3$ and $\|S_k\|=12k$. A denotes the set of all action classes, $a_{t_i}$ denotes the $i_{th}$ action class score for the $t_{th}$ frame from LSTM and $a_{t_i}^*$ denotes the corresponding Ground Truth.

Referring again to FIG. 1, the machine learning back-end unit 135 can utilize custom labelling tools with interfaces optimized for labeling RoI, cycles and action. The labelling tools can include both standalone application built on top of Open source Computer Vision (OpenCV) and web browser application that allow for the labeling of video segment.

Figure 5:
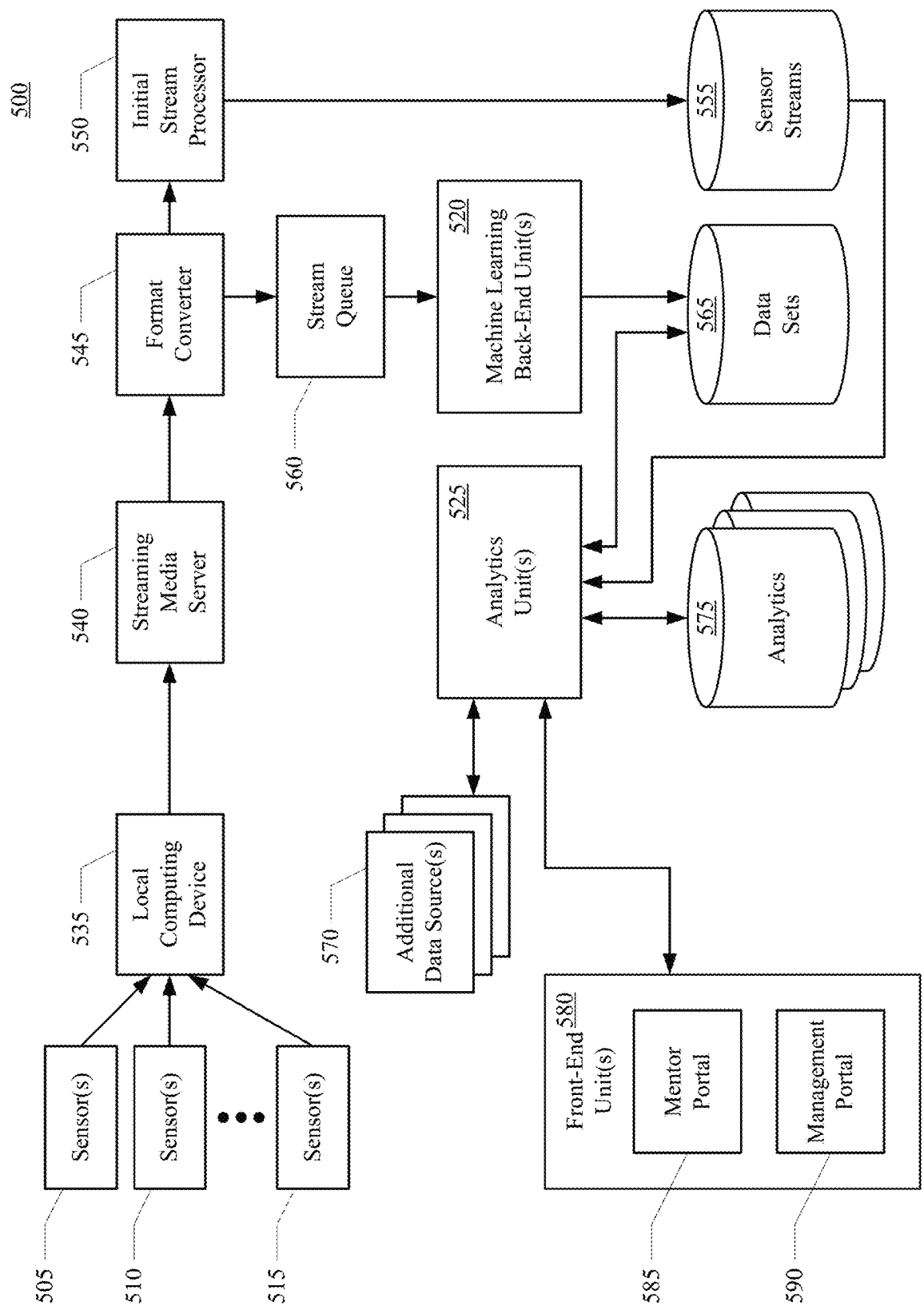
FIG. 5 shows an action recognition and analytics system, in accordance with aspects of the present technology.

Referring now to FIG. 5, an action recognition and analytics system, in accordance with aspect of the present technology, is shown. Again, the action recognition and analytics system 500 can be deployed in a manufacturing, health care, warehousing, shipping, retail, restaurant, or similar context. The system 500 similarly includes one or more sensors 505-515 disposed at one or more stations, one or more machine learning back-end units 520, one or more analytics units 525, and one or more front-end units 530. The one or more sensors 505-515 can be coupled to one or more local computing devices 535 configured to aggregate the sensor data streams from the one or more sensors 505-515 for transmission across one or more communication links to a streaming media server 540. The streaming media server 540 can be configured to received one or more streams of sensor data from the one or more sensors 505-515. A format converter 545 can be coupled to the streaming media server 540 to receive the one or more sensor data streams and convert the sensor data from one format to another. For example, the one or more sensors may generate Motion Picture Expert Group (MPEG) formatted (e.g., H.264) video sensor data, and the format converter 545 can be configured to extract frames of JPEG sensor data. An initial stream processor 550 can be coupled to the format convert 555. The initial stream processor 550 can be configured to segment the sensor data into pre-determined chucks, subdivide the chunks into key frame aligned segment, and create per segment sensor data in one or more formats. For example, the initial stream processor 550 can divide the sensor data into five minute chunks, subdivide the chunks into key frame aligned segment, and convert the key frame aligned segments into MPEG, MPEG Dynamic Adaptive Streaming over Hypertext Transfer Protocol (DASH) format, and or the like. The initial stream processor 550 can be configured to store the sensor stream segments in one or more data structures for storing sensor streams 555. In one implementation, as sensor stream segments are received, each new segment can be appended to the previous sensor stream segments stored in the one or more data structures for storing sensor streams 555.

Figure 6:
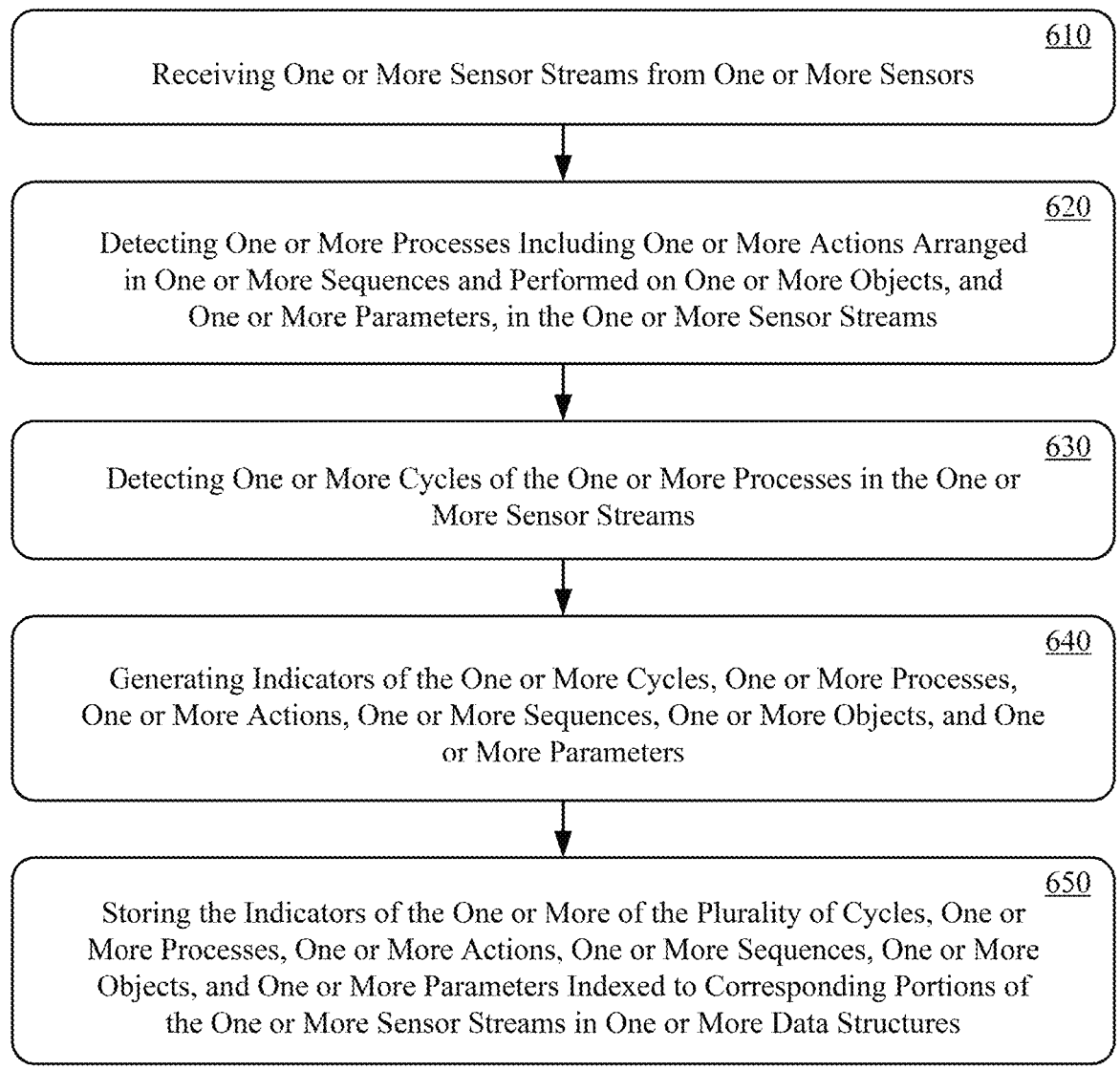
FIG. 6 shows an exemplary method of detecting actions, in accordance with aspects of the present technology.

A stream queue 560 can also be coupled to the format converter 545. The stream queue 560 can be configured to buffer the sensor data from the format converter 545 for processing by the one or more machine learning back-end units 520. The one or more machine learning back-end units 520 can be configured to recognize, in real time, one or more cycles, processes, actions, sequences, objects, parameters and the like in the sensor streams received from the plurality of sensors 505-515. Referring now to FIG. 6, an exemplary method of detecting actions, in accordance with aspects of the present technology, is shown. The action recognition method can include receiving one or more sensor streams from one or more sensors, at 610. In one implementation, one or more machine learning back-end units 520 can be configured to receive sensor streams from sensors 505-515 disposed at one or more stations.

At 620, a plurality of processes including one or more actions arranged in one or more sequences and performed on one or more objects, and one or more parameters can be detected. in the one or more sensor streams. At 630, one or more cycles of the plurality of processes in the sensor stream can also be determined. In one implementation, the one or more machine learning back-end units 520 can recognize cycles, processes, actions, sequences, objects, parameters and the like in sensor streams utilizing deep learning, decision tree learning, inductive logic programming, clustering, reinforcement learning, Bayesian networks, and or the like.

At 640, indicators of the one or more cycles, one or more processes, one or more actions, one or more sequences, one or more objects, and one or more parameters can be generated. In one implementation, the one or more machine learning back-end units 520 can be configured to generate indicators of the one or more cycles, processes, actions, sequences, objects, parameters and or the like. The indicators can include descriptions, identifiers, values and or the like associated with the cycles, processes, actions, sequences, objects, and or parameters. The parameters can include, but is not limited to, time, duration, location (e.g., x, y, z, t), reach point, motion path, grid point, quantity, sensor identifier, station identifier, and bar codes.

At 650, the indicators of the one or more cycles, one or more processes, one or more actions, one or more sequences, one or more objects, and one or more parameters indexed to corresponding portions of the sensor streams can be stored in one or more data structures for storing data sets 565. In one implementation, the one or more machine learning back-end units 520 can be configured to store a data set including the indicators of the one or more processes, one or more actions, one or more sequences, one or more objects, and one or more parameters for each cycle. The data sets can be stored in one or more data structures for storing the data sets 565. The indicators of the one or more cycles, one or more processes, one or more actions, one or more sequences, one or more objects, and one or more parameters in the data sets can be indexed to corresponding portion of the sensor streams in one or more data structures for storing sensor streams 555.

In one implementation, the one or more streams of sensor data and the indicators of the one or more of the plurality of cycles, one or more processes, one or more actions, one or more sequences, one or more objects and one or more parameters indexed to corresponding portion of the one or more streams of sensor data can be encrypted when stored to protect the integrity of the streams of sensor data and or the data sets. In one implementation, the one or more streams of sensor data and the indicators of the one or more of the plurality of cycles, one or more processes, one or more actions, one or more sequences, one or more objects and one or more parameters indexed to corresponding portion of the one or more streams of sensor data can be stored utilizing block chaining. The blockchaining can be applied across the cycles, sensor streams, stations, supply chain and or the like. The blockchaining can include calculating a cryptographic hash based on blocks of the data sets and or blocks of the streams of sensor data. The data sets, streams of sensor data and the cryptographic hash can be stored in one or more data structures in a distributed network.

Referring again to FIG. 5, the one or more analytics units 525 can be coupled to the one or more data structures for storing the sensor streams 555, one or more data structures for storing the data set 565, one or more additional sources of data 570, one or more data structures for storing analytics 575. The one or more analytics units 525 can be configured to perform statistical analysis on the cycle, process, action, sequence, object and parameter data in one or more data sets. The one or more analytics units 525 can also utilize additional data received from one or more additional data sources 570. The additional data sources 570 can include, but are not limited to, Manufacturing Execution Systems (MES), warehouse management system, or patient management system, accounting systems, robot datasheets, human resource records, bill of materials, and sales systems. Some examples of data that can be received from the additional data sources 570 can include, but is not limited to, time, date, shift, day of week, plant, factory, assembly line, sub-assembly line, building, room, supplier, work space, action capability, and energy consumption, ownership cost. The one or more analytics units 525 can be configured to utilize the additional data from one or more additional source of data 570 to update, correct, extend, augment or the like, the data about the cycles, processes, action, sequences, objects and parameters in the data sets. Similarly, the additional data can also be utilized to update, correct, extend, augment or the like, the analytics generate by the one or more analytics front-end units 525. The one or more analytics units 525 can also store trends and other comparative analytics utilizing the data sets and or the additional data, can use sensor fusion to merge data from multiple sensors, and other similar processing and store the results in the one or more data structures for storing analytics 575. In one implementation, one or more engines 170, such as the one or more machine learning back-end units 520 and or the one or more analytics units 525, can create a data structure including a plurality of data sets, the data sets including one or more indicators of at least one of one or more cycles, one or more processes, one or more actions, one or more sequences, one or more object and one or more parameters. The one or more engine 170 can build the data structure based on the one of one or more cycles, one or more processes, one or more actions, one or more sequences, one or more object and one or more parameters detected in the one or more sensor streams. The data structure definition, configuration and population can be performed in real time based upon the content of the one or more sensor streams. For example, Table 1 shows a table defined, configured and populated as the sensor streams are processed by the one or more machine learning back-end unit 520.

TABLE 1

ENTITY ID DATA STUCTURE (TABLE 1)

| FRAME | HUMAN | HAND | ARM | LEG | MOTHER-BOARD | SCREW |
|-------|-------|------|-----|-----|--------------|-------|
| 1 | Yes | Yes | Yes | Yes | YES | Yes |
| 2 | Yes | No | No | Yes | Yes | No |
| 3 | Yes | Yes | Yes | Yes | YES | Yes |

The data structure creation process can continue to expand upon the initial structure and or create additional data structures base upon additional processing of the one or more sensor streams.

In one embodiment, the status associated with entities is added to a data structure configuration (e.g., engaged in an action, subject to a force, etc.) based upon processing of the access information. In one embodiment, activity associated with the entities is added to a data structure configuration (e.g., engaged in an action, subject to a force, etc.) based upon processing of the access information. One example of entity status data set created from processing of above entity ID data set (e.g., motion vector analysis of image object, etc.) is illustrated in Table 2.

TABLE 2

ENTITY STATUS DATA STRUCTURE

| FRAME | HAND MOVING | ARM MOVING | LEG MOVING | HUMAN MOVING |
|-------|-------------|------------|------------|--------------|
| 1 | Yes | Yes | No | Yes |
| 2 | No | No | Yes | No |
| 3 | Yes | Yes | Yes | Yes |

In one embodiment, a third-party data structure as illustrated in Table 3 can be accessed.

TABLE 3

OSHA DATA STRUCTURE

| ACTIVITY | SAFE TO MOVE LEG | SAFE TO MOVE HAND |
|----------|------------------|-------------------|
| SCREWING TO MOTHERBOARD | No | Yes |
| LIFTING HOUSING | Yes | Yes |

In one embodiment, activity associated with entities is added to a data structure configuration (e.g., engaged in an action, subject to a force, etc.) based upon processing of the access information as illustrated in Table 4.

TABLE 4

ACTIVITY DATA STRUCTURE

| FRAME | SCREWING TO MOTHERBOARD | HUMAN ACTION SAFE | MOTHERBOARD COMPLETE |
|---|---|---|---|
| 1 | Yes | Yes | Yes |
| 2 | No | NA | NO |
| 3 | Yes | NO | Yes |

Table 4 is created by one or more engines 170 based on further analytics/processing of info in Table 1, Table 2 and Table 3. In one example, Table 4 is automatically configured to have a column for screwing to motherboard. In frames 1 and 3 since hand is moving (see Table 2) and screw present (see Table 1), then screwing to motherboard (see Table 3). In frame 2, since hand is not moving (see Table 2) and screw not present (see Table 1), then no screwing to motherboard (see Table 3).

Table 4 is also automatically configured to have a column for human action safe. In frame 1 since leg not moving in frame (see Table 2) the worker is safely (see Table 3) standing at workstation while engage in activity of screwing to motherboard. In frame 3 since leg moving (see Table 2) the worker is not safely (see Table 3) standing at workstation while engage in activity of screwing to motherboard.

The one or more analytics units 525 can also be coupled to one or more front-end units 580. The one or more front-end units 580 can include a mentor portal 585, a management portal 590, and other similar portals. The mentor portal 585 can be configured for presenting feedback generated by the one or more analytics units 525 and or the one or more front-end units 580 to one or more actors. For example, the mentor portal 585 can include a touch screen display for indicating discrepancies in the processes, actions, sequences, objects and parameters at a corresponding station. The mentor portal 585 could also present training content generated by the one or more analytics units 525 and or the one or more front-end units 580 to an actor at a corresponding station. The management port 590 can be configured to enable searching of the one or more data structures storing analytics, data sets and sensor streams. The management port 590 can also be utilized to control operation of the one or more analytics units 525 for such functions as generating training content, creating work charts, performing line balancing analysis, assessing ergonomics, creating job assignments, performing causal analysis, automation analysis, presenting aggregated statistics, and the like.

The action recognition and analytics system 500 can non-intrusively digitize processes, actions, sequences, objects, parameters and the like performed by numerous entities, including both humans and machines, using machine learning. The action recognition and analytics system 500 enables human activity to be measured automatically, continuously and at scale. By digitizing the performed processes, actions, sequences, objects, parameters, and the like, the action recognition and analytics system 500 can optimize manual and/or automatic processes. In one instance, the action recognition and analytics system 500 enables the creation of a fundamentally new data set of human activity. In another instance, the action recognition and analytics system 500 enables the creation of a second fundamentally new data set of man and machine collaborating in activities. The data set from the action recognition and analytics system 500 includes quantitative data, such as which actions were performed by which person, at which station, on which specific part, at what time. The data set can also include judgements based on performance data, such as does a given person perform better or worse that average. The data set can also include inferences based on an understanding of the process, such as did a given product exited the assembly line with one or more incomplete tasks.

Figure 7:
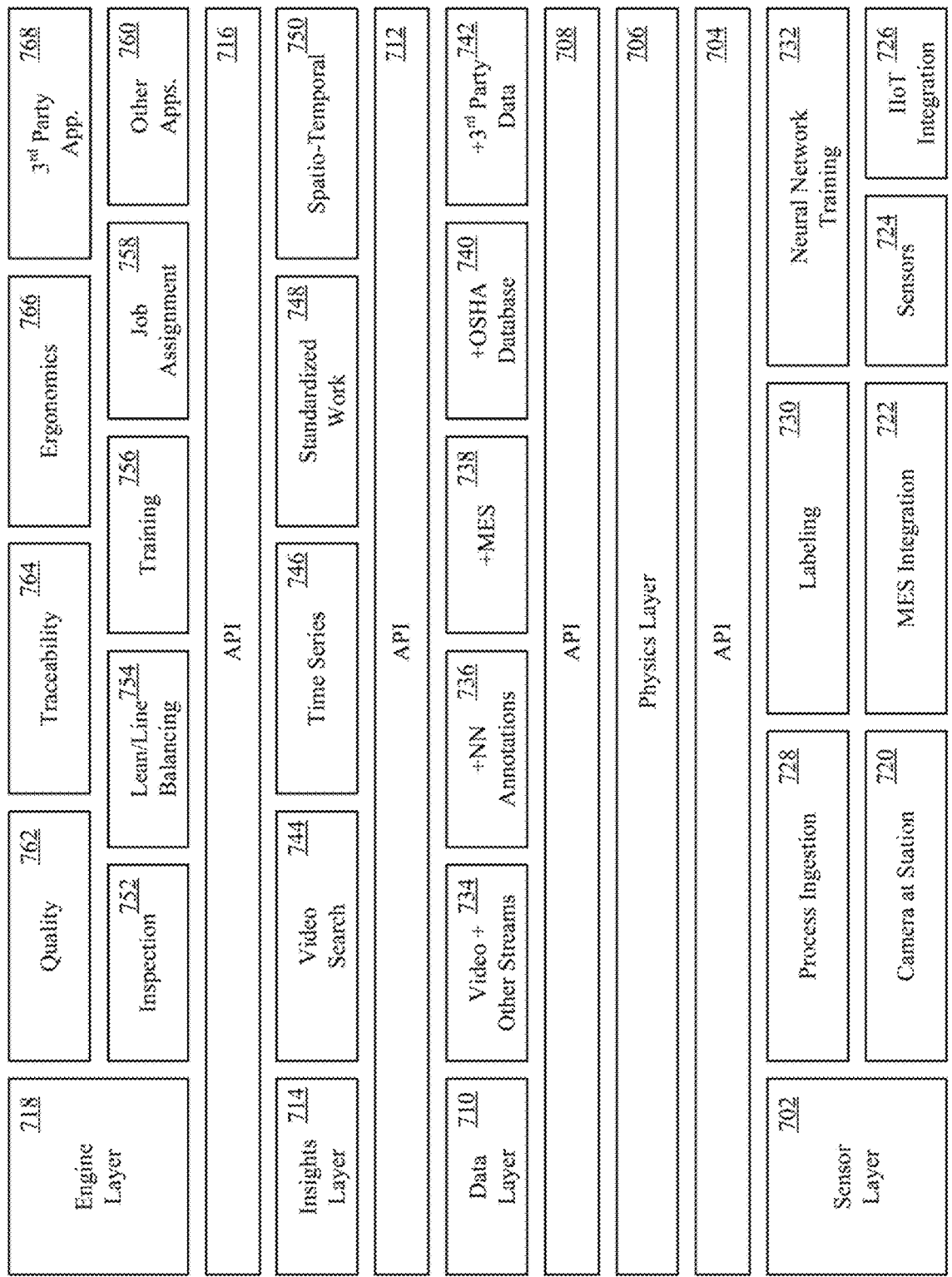
FIG. 7 shows an action recognition and analytics system, in accordance with aspects of the present technology.

Referring now to FIG. 7, an action recognition and analytics system, in accordance with aspects of the present technology, is shown. The action recognition and analytics system can include a plurality of sensor layers 702, a first Application Programming Interface (API) 704, a physics layer 706, a second API 708, a plurality of data 710, a third API 712, a plurality of insights 714, a fourth API 716 and a plurality of engine layers 718. The sensor layer 702 can include, for example, cameras at one or more stations 720, MES stations 722, sensors 724, IIoT integrations 726, process ingestion 728, labeling 730, neural network training 732 and or the like. The physics layer 706 captures data from the sensor layer 702 to passes it to the data layer 710. The data layer 710, can include but not limited to, video and other streams 734, +NN annotations 736, +MES 738, +OSHA database 740, and third-party data 742. The insights layer 714 can provide for video search 744, time series data 746, standardized work 748, and spatio-temporal 750. The engine layer 718 can be utilized for inspection 752, lean/line balancing 754, training 756, job assignment 758, other applications 760, quality 762, traceability 764, ergonomics 766, and third party applications 768.

Figure 8:
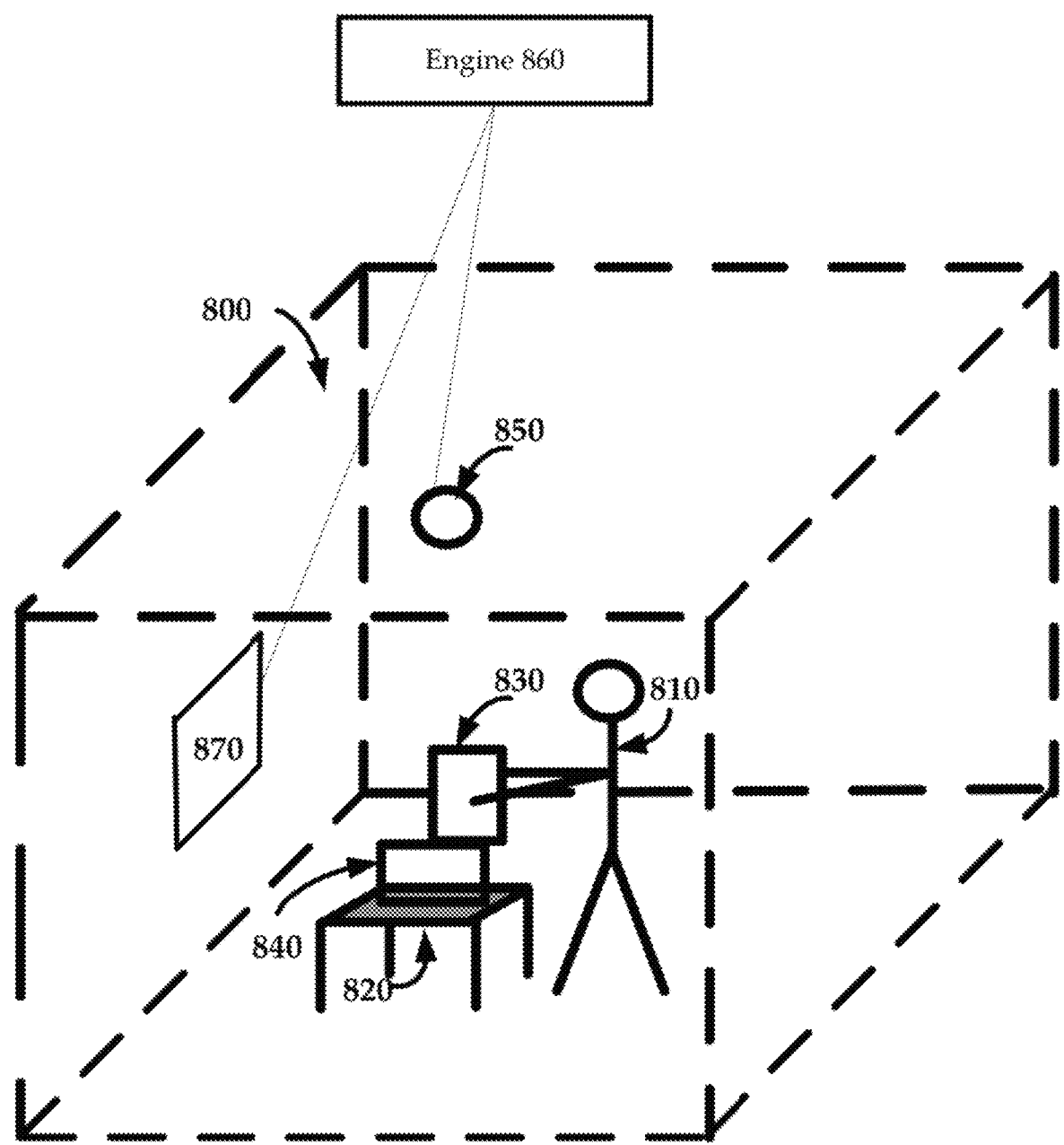
FIG. 8 shows an exemplary station, in accordance with aspects of the present technology

Referring now to FIG. 8, an exemplary station, in accordance with aspects of the present technology, is shown. The station 800 is an areas associated with one or more cycles, processes, actions, sequences, objects, parameters and or the like, herein also referred to as activity. Information regarding a station can be gathered and analyzed automatically. The information can also be gathered and analyzed in real time. In one exemplary implementation, an engine participates in the information gathering and analysis. The engine can use Artificial Intelligence to facilitate the information gathering and analysis. It is appreciated there can be many different types of stations with various associated entities and activities. Additional descriptions of stations, entities, activities, information gathering, and analytics are discussed in other sections of this detailed description.

A station or area associated with an activity can include various entities, some of which participate in the activity within the area. An entity can be considered an actor, an object, and so on. An actor can perform various actions on an object associated with an activity in the station. It is appreciated a station can be compatible with various types of actors (e.g., human, robot, machine, etc.). An object can be a target object that is the target of the action (e.g., thing being acted on, a product, a tool, etc.). It is appreciated that an object can be a target object that is the target of the action and there can be various types of target objects (e.g., component of a product or article of manufacture, an agricultural item, part of a thing or person being operated on, etc.). An object can be a supporting object that supports (e.g., assists, facilitates, aids, etc.) the activity. There can be various types of supporting objects, including load bearing components (e.g., a work bench, conveyor belt, assembly line, table top etc.), a tool (e.g., drill, screwdriver, lathe, press, etc.), a device that regulates environmental conditions (e.g., heating ventilating and air conditioning component, lighting component, fire control system, etc.), and so on. It is appreciated there can be many different types of stations with a various entities involved with a variety of activities.

Additional descriptions of the station, entities, and activities are discussed in other sections of this detailed description.

The station 800 can include a human actor 810, supporting object 820, and target objects 830 and 840. In one embodiment, the human actor 810 is assembling a product that includes target objects 830, 840 while supporting object 820 is facilitating the activity. In one embodiment, target objects 830, 840 are portions of a manufactured product (e.g., a motherboard and a housing of an electronic component, a frame and a motor of a device, a first and a second structural member of an apparatus, legs and seat portion of a chair, etc.). In one embodiment, target objects 830, 840 are items being loaded in a transportation vehicle. In one embodiment, target objects 830, 840 are products being stocked in a retail establishment. Supporting object 820 is a load bearing component (e.g., a work bench, a table, etc.) that holds target object 840 (e.g., during the activity, after the activity, etc.). Sensor 850 senses information about the station (e.g., actors, objects, activities, actions, etc.) and forwards the information to one or more engines 860. Sensor 850 can be similar to sensor 135. Engine 860 can include a machine learning back end component, analytics, and front end similar to machine learning back end unit 180, analytics unit 190, and front end 190. Engine 860 performs analytics on the information and can forward feedback to feedback component 870 (e.g., a display, speaker, etc.) that conveys the feedback to human actor 810.

Figure 9:
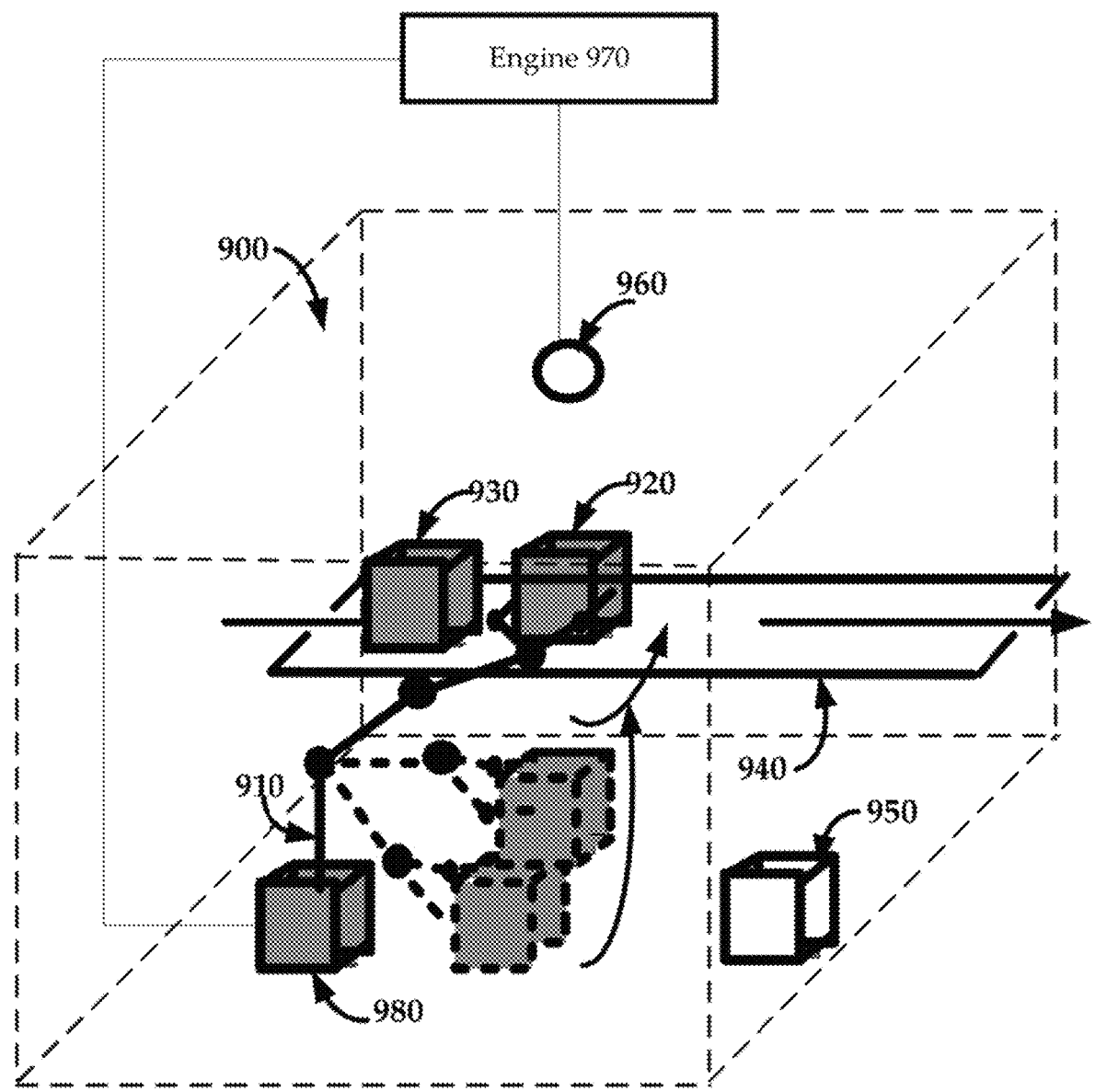
FIG. 9 shows an exemplary station, in accordance with aspects of the present technology

Referring now to FIG. 9, an exemplary station, in accordance with aspects of the present technology, is shown. The station 900 includes a robot actor 910, target objects 920, 930, and supporting objects 940, 950. In one embodiment, the robot actor 910 is assembling target objects 920, 930 and supporting objects 940, 950 are facilitating the activity. In one embodiment, target objects 920, 930 are portions of a manufactured product. Supporting object 940 (e.g., an assembly line, a conveyor belt, etc.) holds target objects 920, 930 during the activity and moves the combined target object 920, 930 to a subsequent station (not shown) after the activity. Supporting object 940 provides area support (e.g., lighting, fan temperature control, etc.). Sensor 960 senses information about the station (e.g., actors, objects, activities, actions, etc.) and forwards the information to engine 970. Engine 970 performs analytics on the information and forwards feedback to a controller 980 that controls robot 910. Engine 970 can be similar to engine 170 and sensor 960 can be similar to sensor 135.

A station can be associated with various environments. The station can be related to an economic sector. A first economic sector can include the retrieval and production of raw materials (e.g., raw food, fuel, minerals, etc.). A second economic sector can include the transformation of raw or intermediate materials into goods (e.g., manufacturing products, manufacturing steel into cars, manufacturing textiles into clothing, etc.). A third sector can include the supply and delivery of services and products (e.g., an intangible aspect in its own right, intangible aspect as a significant element of a tangible product, etc.) to various parties (e.g., consumers, businesses, governments, etc.). In one embodiment, the third sector can include sub sectors. One sub sector can include information and knowledge-based services. Another sub sector can include hospitality and human services. A station can be associated with a segment of an economy (e.g., manufacturing, retail, warehousing, agriculture, industrial, transportation, utility, financial, energy, healthcare, technology, etc,). It is appreciated there can be many different types of stations and corresponding entities and activities. Additional descriptions of the station, entities, and activities are discussed in other sections of this detailed description.

Figure 10:
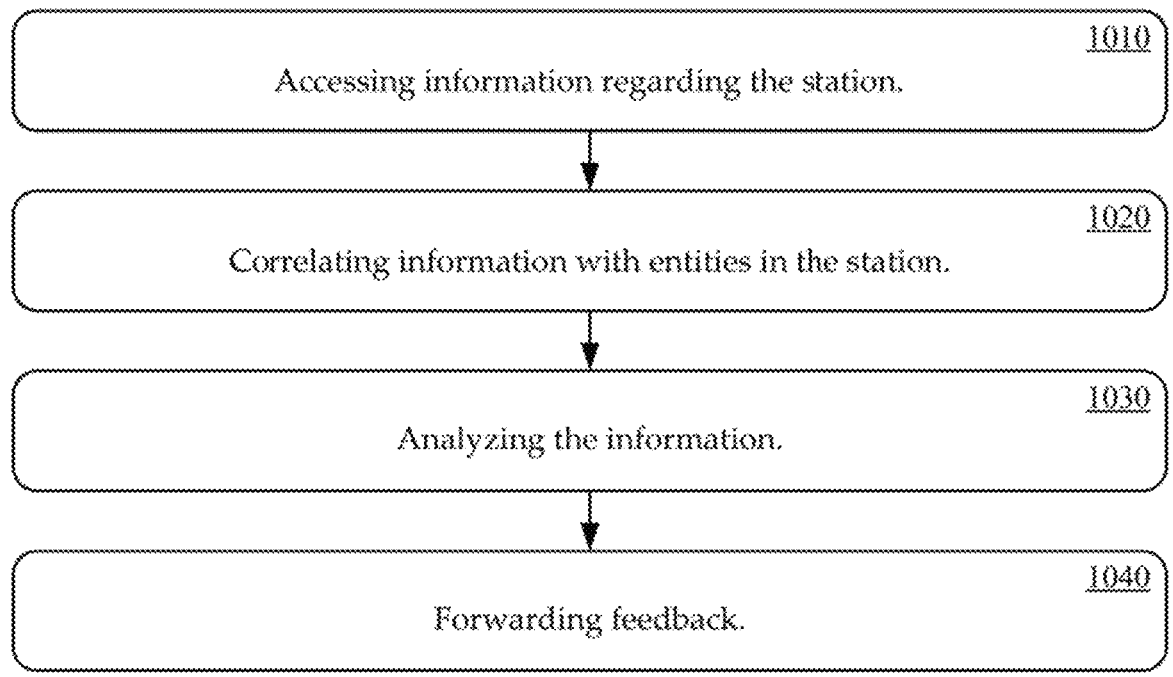
FIG. 10 shows an exemplary station activity analysis method, in accordance with one embodiment.

In one embodiment, station information is gathered and analyzed. In one exemplary implementation, an engine (e.g., an information processing engine, a system control engine, an Artificial Intelligence engine, etc.) can access information regarding the station (e.g., information on the entities, the activity, the action, etc.) and utilizes the information to perform various analytics associated with the station. In one embodiment, engine can include a machine learning back end unit, analytics unit, front end unit, and data storage unit similar to machine learning back end 180, analytics 185, front end 190 and data storage 175. In one embodiment, a station activity analysis process is performed. Referring now to FIG. 10, an exemplary station activity analysis method, in accordance with one embodiment, is shown.

At 1010, information regarding the station is accessed. In one embodiment, the information is accessed by an engine. The information can be accessed in real time. The information can be accessed from monitors/sensors associated with a station. The information can be accessed from an information storage repository. The information can include various types of information (e.g., video, thermal, optical, etc.). Additional descriptions of the accessing information are discussed in other sections of this detailed description At 1020, information is correlated with entities in the station and optionally with additional data sources. In one embodiment, the information the correlation is established at least in part by an engine. The engine can associate the accessed information with an entity in a station. An entity can include an actor, an object, and so on. Additional descriptions of the correlating information with entities are discussed in other sections of this detailed description.

At 1030, various analytics are performed utilizing the accessed information at 1010, and correlations at 1020. In one embodiment, an engine utilizes the information to perform various analytics associated with station. The analytics can be directed at various aspects of an activity (e.g., validation of actions, abnormality detection, training, assignment of actor to an action, tracking activity on an object, determining replacement actor, examining actions of actors with respect to an integrated activity, automatic creation of work charts, creating ergonomic data, identify product knitting components, etc.) Additional descriptions of the analytics are discussed in other sections of this detailed description.

At 1040, optionally, results of the analysis can be forwarded as feedback. The feedback can include directions to entities in the station. In one embodiment, the information accessing, analysis, and feedback are performed in real time. Additional descriptions of the station, engine, entities, activities, analytics and feedback are discussed in other sections of this detailed description, It is also appreciated that accessed information can include general information regarding the station (e.g., environmental information, generic identification of the station, activities expected in station, a golden rule for the station, etc.). Environmental information can include ambient aspects and characteristics of the station (e.g., temperature, lighting conditions, visibility, moisture, humidity, ambient aroma, wind, etc.).

It also appreciated that some of types of characteristics or features can apply to a particular portion of a station and also the general environment of a station. In one exemplary implementation, a portion of a station (e.g., work bench, floor area, etc.) can have a first particular visibility level and the ambient environment of the station can have a second particular visibility level. It is appreciated that some of types of characteristics or features can apply to a particular entity in a station and also the station environment. In one embodiment, an entity (e.g., a human, robot, target object etc.) can have a first particular temperature range and the station environment can have a second particular temperature range.

The action recognition and analytics system 100, 500 can be utilized for process validation, anomaly detection and/or process quality assurance in real time. The action recognition and analytics system 100, 500 can also be utilized for real time contextual training. The action recognition and analytics system 100, 500 can be configured for assembling training libraries from video clips of processes to speed new product introductions or onboard new employees. The action recognition and analytics system 100, 500 can also be utilized for line balancing by identifying processes, sequences and/or actions to move among stations and implementing lean processes automatically. The action recognition and analytics system 100, 500 can also automatically create standardized work charts by statistical analysis of processes, sequences and actions. The action recognition and analytics system 100, 500 can also automatically create birth certificate videos for a specific unit. The action recognition and analytics system 100, 500 can also be utilized for automatically creating statistically accurate ergonomics data. The action recognition and analytics system 100, 500 can also be utilized to create programmatic job assignments based on skills, tasks, ergonomics and time. The action recognition and analytics system 100, 500 can also be utilized for automatically establishing traceability including for causal analysis. The action recognition and analytics system 100, 500 can also be utilized for kitting products, including real time verification of packing or unpacking by action and image recognition. The action recognition and analytics system 100, 500 can also be utilized to determine the best robot to replace a worker when ergonomic problems are identified. The action recognition and analytics system 100, 500 can also be utilized to design an integrated line of humans and cobot and/or robots. The action recognition and analytics system 100, 500 can also be utilized for automatically programming robots based on observing non-modeled objects in the work space.

Figure 11A:
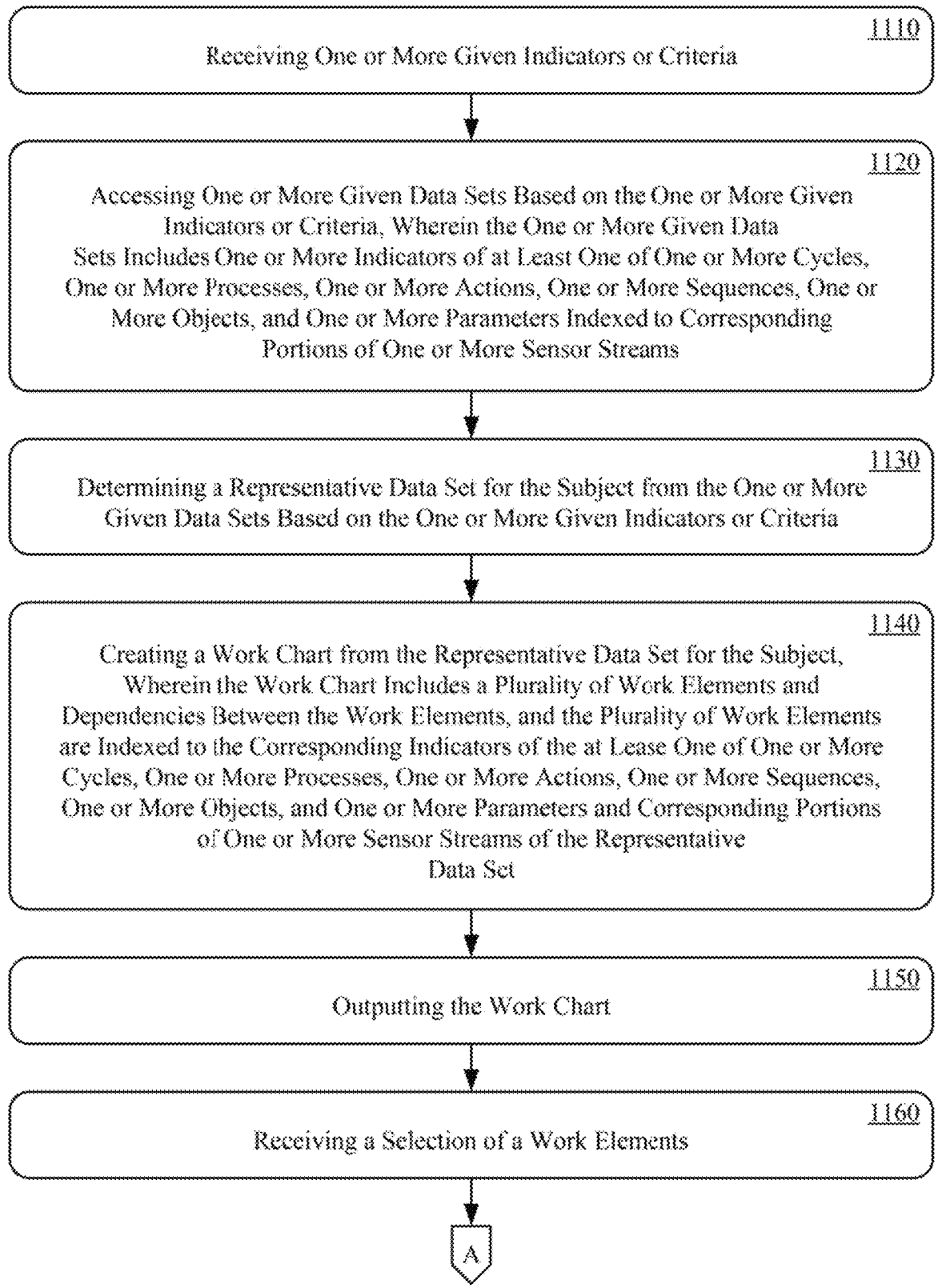
FIGS. 11A and 11B show a method of creating work charts, in accordance with aspects of the present technology.
Figure 11B:
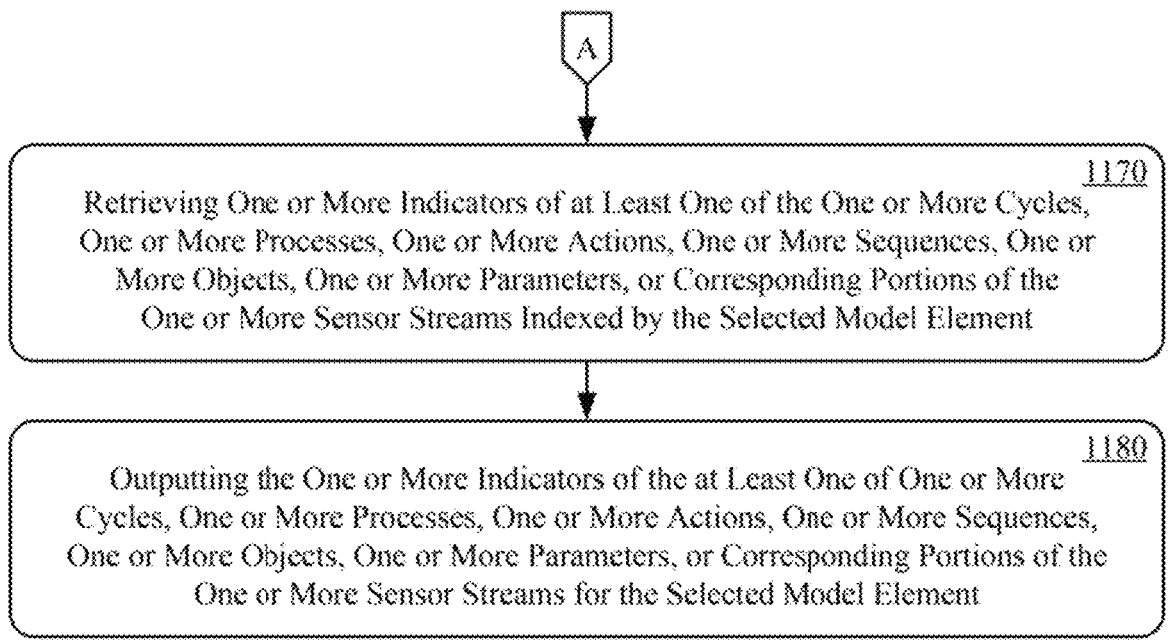

Referring now to FIGS. 11A and 11B, a method of creating work charts, in accordance with aspects of the present technology, is shown. The method can include receiving one or more given indicators or criteria, at 1110. In one implementation, the one or more engines 170 can receive one or more indicators or criteria, such as a given time period, an average duration, a fasters duration for the cycles or for a given task, a slowest duration for the cycles or a given task, a distribution, a line identifier, a worker identifier, a distribution of a sequence and or the like.

At 1120, one or more given data sets can be accessed based on the one or more given indicators or criteria. The data sets can include one or more indicators of at least one of one or more cycles, one or more processes, one or more actions, one or more sequences, one or more objects, and one or more parameters in one or more sensor streams for a subject. The subject can include an article of manufacture, a health care service, warehousing transaction, a shipping transaction, a retail transaction, or the like. In one implementation, the one or more indicators of at least one of one or more cycles, one or more processes, one or more actions, one or more sequences, one or more objects, and one or more parameters of the data sets can be indexed to corresponding portions of one or more sensor streams. In one implementation, one or more engines 170 can be configured to access one or more given data sets stored in one or more data structures on one or more data storage units 175. In one implementation, the data sets and the corresponding portions of one or more sensor streams can be blockchained to protect the integrity of the data. The blockchaining can be applied across the cycles, sensor streams, stations, supply chain and or the like.

At 1130, a representative data set for the subject can be determined from the one or more given data sets based on the one or more given indicators or criteria. The representative data set can include one or more indicators of at least one of one or more cycles, one or more processes, one or more actions, one or more sequences, one or more objects, and one or more parameters of the subject satisfying one or more of the given parameters or criteria. In one implementation, the one or more engines 170 can be configured to statistically analyze the one or more given data sets to determine the representative data set for the subject.

At 1140, a work chart for the subject can be created from the representative data set. The work chart can include a plurality of work elements and dependencies between the work elements. In one implementation, the one or more engines 170 can be configured to create the work chart from the one or more indicators of at least one of one or more cycles, one or more processes, one or more actions, one or more sequences, one or more objects, and one or more parameters of the representative data set. In one implementation, the plurality of work elements and dependencies between the work elements can be indexed to the corresponding indicators of the at least one of one or more cycles, one or more processes, one or more actions, one or more sequences, one or more objects, and one or more parameters of the representative data set.

At 1150, the work chart can be output. In one implementation, the one or more engines 170 can be configured to out the work chart in a graphics user interface for display to a user. In one implementation, the work chart can be created for any, every or a selection of cycles. For example, a work chart can be created for a selection of cycles in a given time period specified by the received one or more given indicators or criteria. In another example, a work chart can be created for every sequence detected in the one or more sensor streams. In another example, a chart can be created based on an average duration of cycles, processes, sequences and or actions. In yet another example, a chart can be created for a fastest or slowest possible duration for a cycle or each task. In addition, a work chart can be created to show a distribution of different sequences of tasks in a plot. For example, a long-tail of a distribution can show that given sequences are followed, whereas equal distribution shows no one sequence is followed by a majority of workers. A most or least efficient sequence performed can be identified from the distribution. Similarly, a sequence with the most deviation can be identified.

Figure 12:
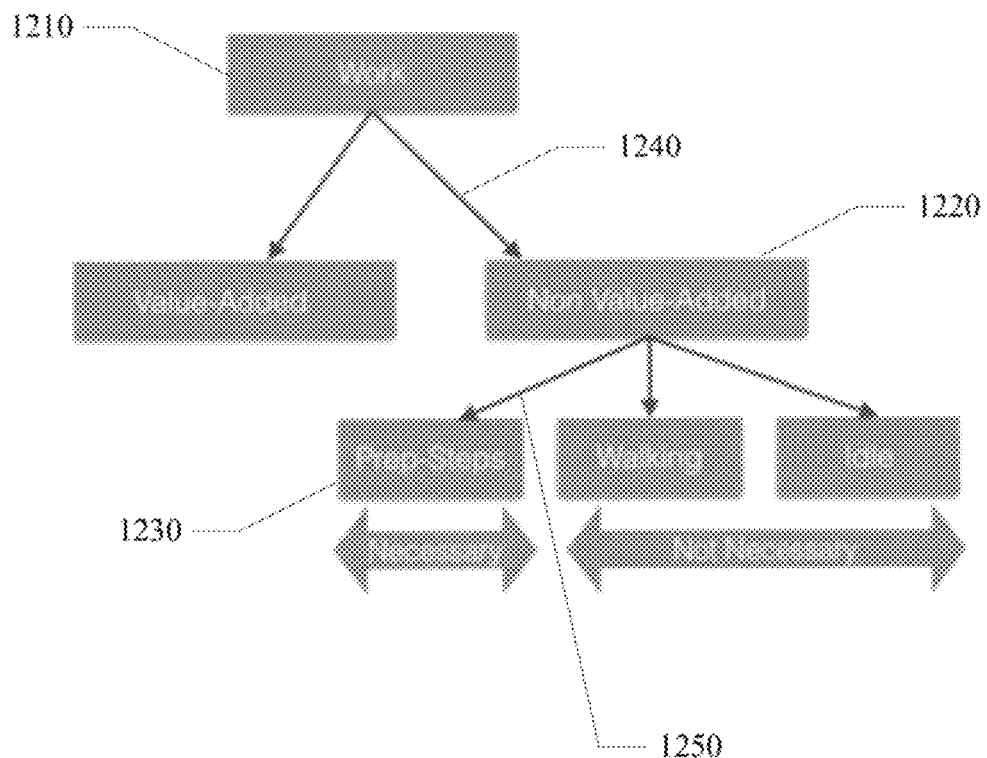
FIG. 12 shows an exemplary work chart, in accordance with aspects of the present technology.

Referring now to FIG. 12, an exemplary work chart, in accordance with aspects of the present technology, is shown. As illustrate, the work chart can include a plurality of work element 1210-1230 and dependencies 1240, 1250 between the work elements 1210-1230. In one implementation, the work chart can be organized based on a lean framework. The lean work chart can include work that can be characterized as value added work and nonvalue added work. The non-value-added work can include necessary, walking and idle. Value added work can be work which adds value to the subject. Non-value added, but necessary work, can be work that does not add value to the end subject but is necessary.

A non-value-added walking work can be the work of moving between machines or between areas of a station. Non-value-added idle work can be work that neither adds value to the end subject, nor is necessary to be able to provide the end subject. Various types of delays, such as late shipments, are example of non-value-added idle work. Non-value-added idle work should be eliminated or reduced whenever possible. In accordance with aspects of the present technology, the work charts can be based on statistical data derived from one or more sensor streams over many cycles that capture data tens of time a second. The resolution, accuracy and breadth of the data from the one or more sensor streams allow the processes to be constantly adjusted to gain efficiencies in fields where even a small decimal percentage increase can be a big win.

Figure 13:
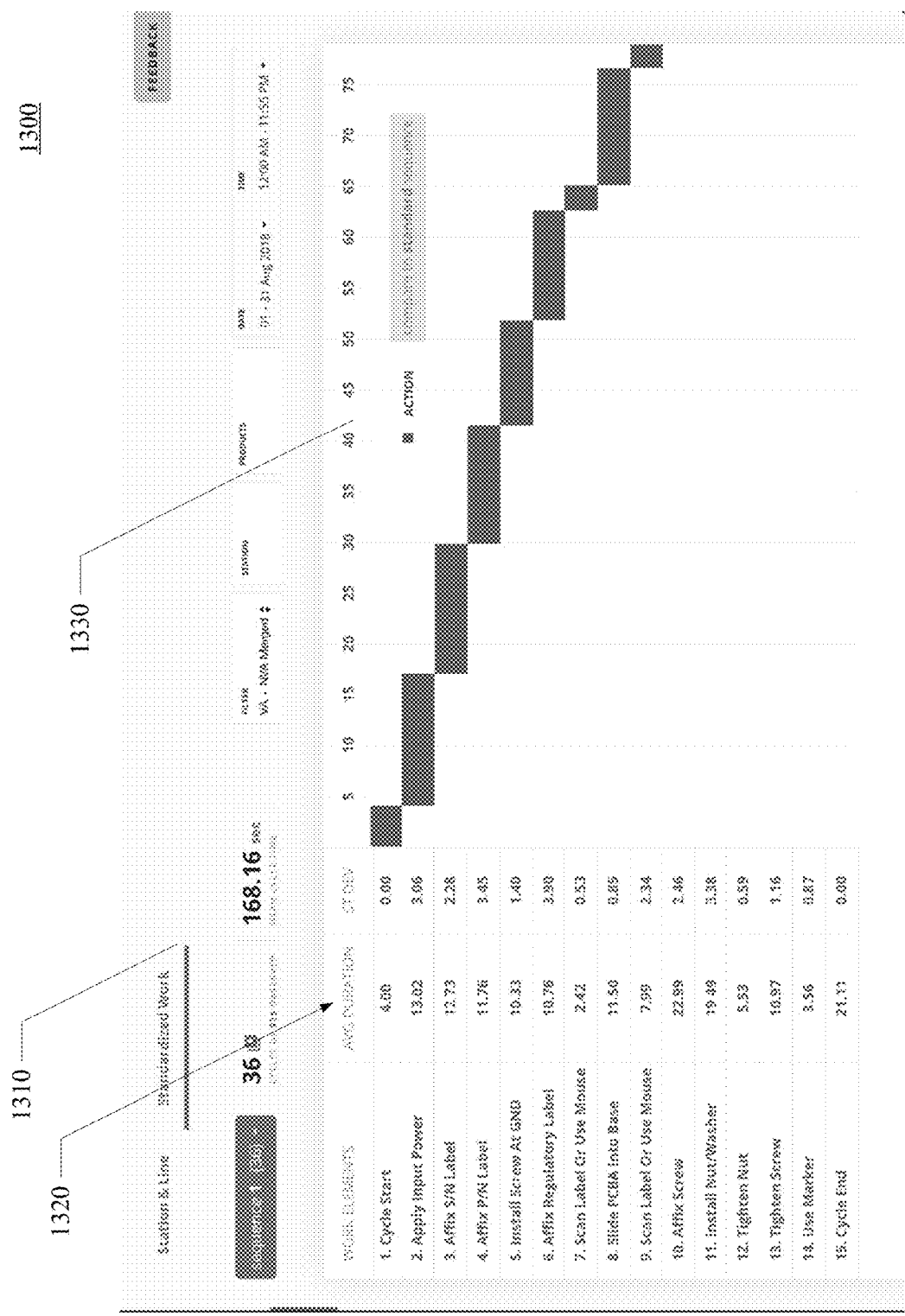
FIG. 13 shows another an exemplary work chart, in accordance with aspects of the present technology.

Referring now to FIG. 13, an exemplary work chart, in accordance with aspects of the present technology is shown. The work chart can be a standardized work chart, which illustrates the progress through a cycle of one or more processes, one or more actions, one or more sequences, one or more objects, and or one or more parameters including the associated time. The horizontal direction can represent the time required for tasks and the vertical direction can represent the time between tasks. Statistical values, such as mean and standard deviation, can be calculated for each step. These times can then be compared to the time available to complete a task to meet production requirements (takt). The standardized work chart provides a way to visualize a process to determine where and how much improvement can be made.

Referring again to FIGS. 11A and 11B, the work charting method can further include receiving a selection of a work element, at 1160. In one implementation, the one or more engines 170 can be configured to receive a selection of a given work element of the work chart. For example, a user can click on a given work element in a graphical user interface.

At 1170, one or more indicators of at least one of the one or more cycles, one or more processes, one or more actions, one or more sequences, one or more objects, one or more parameters, and or corresponding portions of the plurality of sensor streams indexed by the selected model element can be retrieved. In one implementation, the engine 170 can be configured to access one or more data structures in one or more data storage units 175 to retrieve one or more cycles, processes, actions, sequences, objects and or parameters of the representative data set indexed by the selected model element. The one or more engines 170 can also be configured to access one or more data structures in the one or more data storage units 175 to retrieve corresponding portions of one or more sensor streams indexed by the one or more cycles, one or more processes, one or more actions, one or more sequences, one or more objects, and one or more parameters of the representative data set.

At 1180, the one or more indicators of at least one of the one or more of the one or more cycles, one or more processes, one or more actions, one or more sequences, one or more objects, one or more parameters, and or corresponding portions of the plurality of sensor streams can be output for the selected model element. In one implementation, the one or more engines 170 can be configured to output the one or more cycles, one or more processes, one or more actions, one or more sequences, one or more objects, one or more parameters, or corresponding portions of the plurality of sensor streams in the graphics user interface for display to the user.

In aspect, the action recognition and analytics method can create a work chart of an entire assembly process, step by step at each station for every instance of a subject produced. Work charts can also be created based on one or more specified indicators and or criteria. The work chart can also be linked to corresponding indicators of cycles, processes, actions, sequences, objects, parameters and or corresponding portions of sensor streams of a representative instance of a subject.

Figure 14:
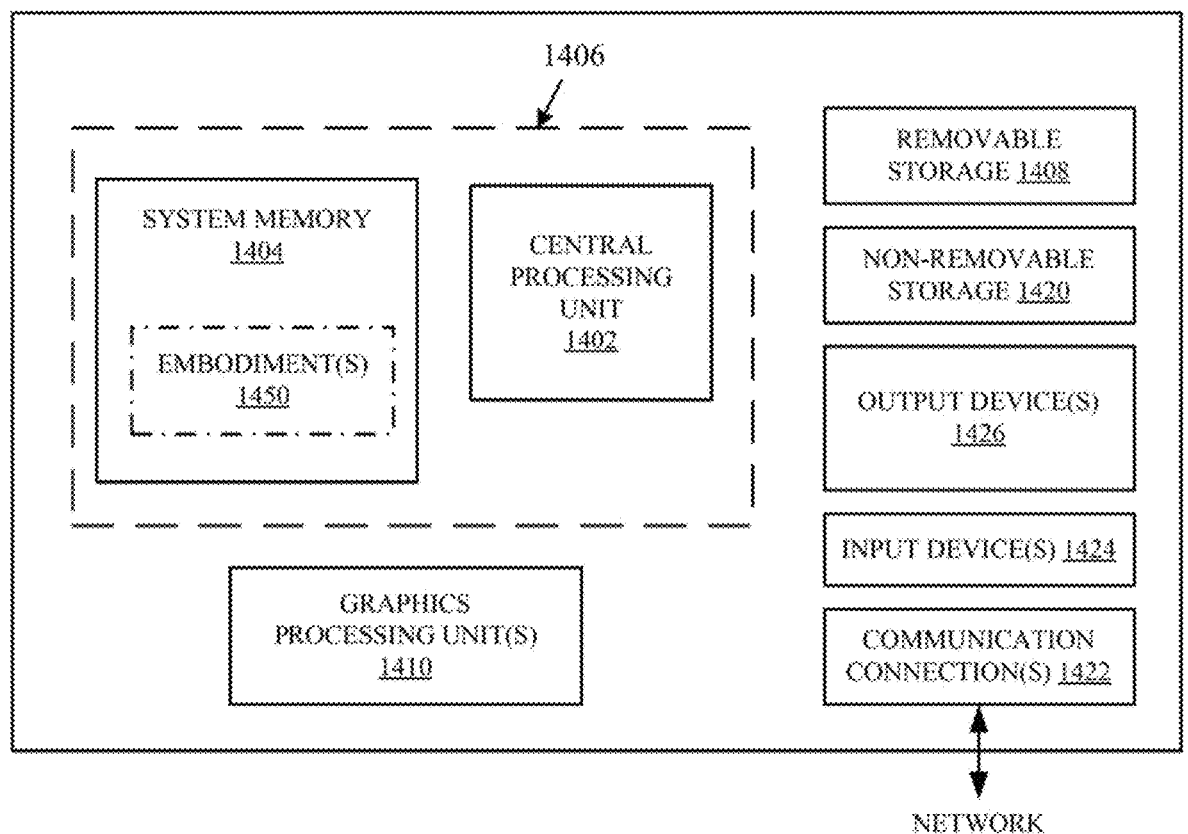
FIG. 14 shows an exemplary computing device, in accordance with aspects of the present technology.

Referring now to FIG. 14, a block diagram of an exemplary computing device upon which various aspects of the present technology can be implemented. In various embodiments, the computer system 1400 may include a cloud-based computer system, a local computer system, or a hybrid computer system that includes both local and remote devices. In a basic configuration, the system 1400 includes at least one processing unit 1402 and memory 1404. This basic configuration is illustrated in FIG. 14 by dashed line 1406. The system 1400 may also have additional features and/or functionality. For example, the system 1400 may include one or more Graphics Processing Units (CPUs) 1410. Additionally, the system 1400 may also include additional storage (e.g., removable and/or non-removable) including, but not limited to, magnetic or optical disks or tape. Such additional storage is illustrated in FIG. 14 by removable storage 1408 and non-removable storage 1420.

The system 1400 may also contain communications connection(s) 1422 that allow the device to communicate with other devices, e.g., in a networked environment using logical connections to one or more remote computers. Furthermore, the system 1400 may also include input device(s) 1424 such as, but not limited to, a voice input device, touch input device, keyboard, mouse, pen, touch input display device, etc. In addition, the system 1400 may also include output device(s) 1426 such as, but not limited to, a display device, speakers, printer, etc.

In the example of FIG. 14, the memory 1404 includes computer-readable instructions, data structures, program modules, and the like associated with one or more various embodiments 1450 in accordance with the present disclosure. However, the embodiments(s) 1450 may instead reside in any one of the computer storage media used by the system 1400, or may be distributed over some combination of the computer storage media, or may be distributed over some combination of networked computers, but is not limited to such.

It is noted that the computing system 1400 may not include all of the elements illustrated by FIG. 14. Moreover, the computing system 1400 can be implemented to include one or more elements not illustrated by FIG. 14. It is pointed out that the computing system 1400 can be utilized or implemented in any manner similar to that described and/or shown by the present disclosure, but is not limited to such.

The foregoing descriptions of specific embodiments of the present technology have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is intended that the scope of the invention be defined by the claims appended hereto and their equivalents.

What is claimed is:

1. A method of creating work charts comprising:
receiving one or more given indicators or criteria including a selection of cycles within a given time period;
accessing one or more given data sets based on the one or more given indicators or criteria, wherein the one or more given data sets include one or more indicators of at least one of one or more cycles, one or more processes, one or more actions, one or more sequences, one or more objects, and one or more parameters of a manufacturing operation of a product determined by convolution neural network deep learning using a computing device executing a machine learning engine over each of a plurality of video frame sensor streams from a plurality of manufacturing stations across an assembly line, wherein the one or more given indicators of the at least one of one or more cycles, one or more processes, one or more actions, one or more sequences, one or more objects, and one or more parameters of the manufacturing operation are indexed to corresponding portions of the plurality of video frame sensor streams, wherein the determination by the convolution neural network deep learning comprises:
performing, with a frame feature extractor, a two-dimensional convolution operation on video frames of the plurality of video frame sensor streams to generate a two-dimensional array of feature vectors;
combining neighboring feature vectors in the two-dimensional array of feature vectors and determining a dynamic region of interest, with a region of interest detector, in a set of the neighboring feature vectors, wherein the region of interest detector and the frame feature extractor share layers of a convolution neural network; and
extracting a feature vector from an area within the dynamic region of interest to analyze with the convolution neural network while discarding remaining feature vectors of the two-dimensional array outside of the dynamic region of interest;
determining, by the computing device executing the machine learning engine, a representative data set including the at least one of one or more cycles, one or more processes, one or more actions, one or more sequences, one or more objects and one or more parameters, and quantitative data, judgement data and inference data statistically derived from the one or more given data sets for the selection of cycles within the given time period;
creating, by the computing device executing the machine learning engine, a work chart from the representative data set, wherein the work chart includes a plurality of work elements and dependencies between the plurality of work elements and associated time for performing the plurality of work elements and associated time between the plurality of work elements for the selection of cycles within the given time period, and wherein the plurality of work elements are indexed to the at least one of one or more cycles, one or more processes, one or more actions, one or more sequences, one or more objects, and one or more parameters of the manufacturing operation of the representative data set and to the corresponding portions of the plurality of video frame sensor streams; and
adjusting the manufacturing operation of the product to gain efficiencies of one or more of the plurality of work elements based on the dependencies between the plurality of work elements and the associated time for performing the plurality of work elements and the associated time between the plurality of work elements in the work chart.

2. The method according to claim 1, wherein a subject of the work chart comprises an article of manufacture, a health care service, a shipping transaction or a retailing transaction.

3. The method according to claim 1, wherein the work chart is organized based on a lean framework including value added and non-value added, wherein the non-value added includes idle, walking and necessary.

4. The method according to claim 1, further comprising:
receiving a selection of a work element;
retrieving the one or more indicators of the at least one of the one or more cycles, one or more processes, one or more actions, one or more sequences, one or more objects, one or more parameters indexed by the selected work element; and
outputting the one or more indicators of the at least one of one or more of the one or more cycles, one or more processes, one or more actions, one or more sequences, one or more objects, one or more parameters, or the corresponding portions of the plurality of video frame sensor streams for the selected work element.

5. The method according to claim 4, further comprising:
retrieving the corresponding portions of the plurality of video frame sensor streams indexed by the selected work element; and
outputting the corresponding portions of the plurality of video frame sensor streams indexed by the selected work element.

6. The method according to claim 1, wherein the one or more given data sets and the corresponding portions of the plurality of video frame sensor streams are blockchained.

7. One or more non-transitory computing device-readable storage mediums storing instructions executable by one or more computing devices to perform an action recognition and analytics method of creating work charts comprising:
receiving one or more given indicators or criteria including a selection of cycles within a given time period;
accessing one or more given data sets based on the one or more given indicators or criteria, wherein the one or more given data sets include one or more indicators of at least one of one or more cycles, one or more processes, one or more actions, one or more sequences, one or more objects, and one or more parameters of a manufacturing operation of a product indexed to corresponding portions of one or more video sensor streams from a plurality of manufacturing stations across an assembly line, wherein the one or more indicators of the at least one of one or more cycles, one or more processes, one or more actions, one or more sequences, one or more objections and one or more parameters are determined by convolution neural network deep learning using a computing device executing a machine learning engine from the one or more video sensor streams, the determination by the convolution neural network deep learning comprising:
performing a two-dimensional convolution operation on the one or more video sensor streams with a frame feature extractor to generate a two-dimensional array of feature vectors;
determining a dynamic region of interest in the two-dimensional array of feature vectors with a region of interest detector, wherein the frame feature extractor and the region of interest extractor share convolution layers in a convolution neural network; and extracting a fixed-size feature vector from an area of the one or more video sensor streams within the dynamic region of interest and analyzing the fixed-size feature vector with the convolution neural network without analyzing an area of the one or more video sensor streams outside the dynamic region of interest;

statistically analyzing, by the computing device executing the machine learning engine, the one or more given data sets based on the one or more given indicators or criteria to determine a representative data set including the at least one of one or more cycles, one or more processes, one or more actions, one or more sequences, one or more objects and one or more parameters, and quantitative data, judgement data and inference data for the selection of cycles within the given time period;

creating, by the computing device executing the machine learning engine, a work chart from the representative data set, wherein the work chart includes a plurality of work elements and dependencies between the plurality of work elements and associated time for performing the plurality of work elements and associated time between the plurality of work elements for the selection of cycles within the given time period, and wherein the plurality of work elements are indexed to the at least one of one or more cycles, one or more processes, one or more actions, one or more sequences, one or more objects, and one or more parameters of the manufacturing operation of the representative data set and to the corresponding portions of the one or more video sensor streams; and adjusting one or more of the plurality of work elements of the manufacturing operation of the product to gain efficiencies based on the dependencies between the plurality of work elements and the associated time for performing the plurality of work elements and the associated time between the plurality of work elements in the work chart.

8. The one or more non-transitory computing device-readable storage mediums storing instructions executable by one or more computing devices to perform the action recognition and analytics method of creating work charts according to claim 7, wherein a subject of the one or more given data sets comprises an article of manufacture, a health care service, a shipping transaction or a retailing transaction.

9. The one or more non-transitory computing device-readable storage mediums storing instructions executable by one or more computing devices to perform the action recognition and analytics method of creating work charts according to claim 7, wherein the work chart is organized based on a lean framework including value added and non-value added.

10. The one or more non-transitory computing device-readable storage mediums storing instructions executable by one or more computing devices to perform the action recognition and analytics method of creating work charts according to claim 9, wherein the non-value added includes idle, walking and necessary.

11. The one or more non-transitory computing device-readable storage mediums storing instructions executable by one or more computing devices to perform the action recognition and analytics method of creating work charts according to claim 7, further comprising:
receiving a selection of a work element; and
outputting the one or more indicators of the at least one of one or more of the one or more cycles, one or more processes, one or more actions, one or more sequences, one or more objects, one or more parameters, or the corresponding portions of the one or more video sensor streams for the selected work element.

12. The one or more non-transitory computing device-readable storage mediums storing instructions executable by one or more computing devices to perform the action recognition and analytics method of creating work charts according to claim 11, wherein the one or more indicators of the corresponding ones of the one or more cycles, the one or more processes, the one or more actions, the one or more sequences, the one or more objects, and the one or more parameters are indexed to the corresponding portions of the one or more video sensor streams by corresponding time stamps.

13. A system comprising:
one or more data storage units;
one or more interfaces;
one or more engines configured to:
receive one or more given indicators or criteria including a selection of cycles within a given time period;
access one or more given data sets stored on the one or more data storage units based on the one or more given indicators or criteria, wherein the one or more given data sets include one or more indicators of at least one of one or more cycles, one or more processes, one or more actions, one or more sequences, one or more objects, and one or more parameters of a manufacturing operation of a product, indexed to corresponding portions of one or more video sensor streams from a plurality of manufacturing stations across an assembly line, wherein the one or more indicators of the at least one of one or more cycles, one or more processes, one or more actions, one or more sequences, one or more objections and one or more parameters are determined by convolution neural network deep learning using a computing device executing a machine learning engine from the one or more video sensor streams, the determination by the convolution network deep learning comprising:
performing, by a frame feature extractor, a two-dimensional convolution operation on the one or more video sensor streams to generate a two-dimensional array of feature vectors;
determining, by a region of interest detector, a dynamic region of interest in the two-dimensional array of feature vectors, wherein the frame feature extractor and the region of interest detector share convolution layers of a convolution neural network; and
analyzing, by a region of interest pooling unit of the convolution neural network, an area of the one or more video sensor streams in an area of the dynamic region of interest and discarding feature vectors of the two-dimensional array of feature vectors outside the area of the dynamic region of interest;
determine, by the computing device executing the machine learning engine, a representative data set from the one or more given data sets based on a statistical analysis of the at least one of one or more cycles, one or more processes, one or more actions, one or more sequences, one or more objects and one or more parameters, and quantitative data, judgement data and inference data for the selection of cycles within the given time period;
create, by the computing device executing the machine learning engine, a work chart from the representative data set, wherein the work chart includes a plurality of work elements and dependencies between the plurality of work elements and associated time for performing the plurality of work elements and associated time between the plurality of work elements for the selection of cycles within the given time period, and wherein the plurality of work elements are indexed to the at least one of one or more cycles, one or more processes, one or more actions, one or more sequences, one or more objects, and one or more parameters of the manufacturing operation of the representative data set and to the corresponding portions of the one or more video sensor streams; and adjust the manufacturing operation of the product to gain efficiencies of one or more of the plurality of work elements based on the dependencies between the plurality of work elements and the associated time for performing the plurality of work elements and the associated time between the plurality of work elements in the work chart.

14. The system of claim 13, wherein the one or more given data sets and the corresponding portions of the one or more video sensor streams are blockchained.

15. The system of claim 13, wherein a subject of the one or more video sensor streams comprises an article of manufacture, a health care service, a shipping transaction or a retailing transaction.

16. The system of claim, 13, wherein the one or more indicators of the at least one of one or more cycles, one or more processes, one or more actions, one or more sequences, one or more objects and one or more parameters are indexed to the corresponding portions of the one or more video sensor streams by corresponding time stamps.

17. The system of claim 13, wherein the work chart is organized based on a lean framework including value added and non-value added.

18. The system of claim 17, wherein the non-value added includes idle, walking and necessary.

19. The system of claim 13, wherein the one or more engines are further configured to:

receive a selection of a work element;

retrieve the one or more indicators of the at least one of the one or more cycles, one or more processes, one or more actions, one or more sequences, one or more objects, one or more parameters and the corresponding portions of the one or more video sensor streams indexed by the selected work element from the one or more given data sets stored on the one or more data storage units; and output the one or more indicators of the at least one of one or more cycles, one or more processes, one or more actions, one or more sequences, one or more objects, one or more parameters, or the corresponding portions of the one or more video sensor streams for the selected work element in a graphical user interface on the one or more interfaces.

\* \* \* \* \*